(12) United States Patent
Basu et al.

(10) Patent No.: US 8,790,901 B2
(45) Date of Patent: Jul. 29, 2014

(54) MICROORGANISMS AND METHODS FOR PRODUCING UNSATURATED FATTY ACIDS

(75) Inventors: Subhayu Basu, Chestnut Hill, MA (US);
Gaozhong Shen, Brighton, MA (US);
Brett Boghigian, Boston, MA (US);
David Young, Cambridge, MA (US);
David Berry, Cambridge, MA (US);
Geoffrey von Maltzahn, Cambridge, MA (US)

(73) Assignee: Pronutria, Inc., Cambridge, MA (US)

( * ) Notice: Subject to any disclaimer, the term of this patent is extended or adjusted under 35 U.S.C. 154(b) by 336 days.

(21) Appl. No.: 13/326,211

(22) Filed: Dec. 14, 2011

(65) Prior Publication Data
US 2012/0116108 A1    May 10, 2012

(51) Int. Cl.
*C12P 7/64*     (2006.01)
*C12N 9/02*    (2006.01)
*C12N 1/20*    (2006.01)

(52) U.S. Cl.
USPC .......................... 435/134; 435/252.3; 435/189

(58) Field of Classification Search
USPC ...................................... 435/134, 189, 252.3
See application file for complete search history.

(56) References Cited

U.S. PATENT DOCUMENTS

| | | | |
|---|---|---|---|
| 6,355,861 | B1 | 3/2002 | Thomas |
| 7,736,884 | B2 | 6/2010 | Gunnarsson |
| 7,777,098 | B2 | 8/2010 | Cirpus |
| 7,871,804 | B2 | 1/2011 | Cirpus |
| 8,071,341 | B2 | 12/2011 | Singh |
| 2007/0264688 | A1 | 11/2007 | Venter et al. |
| 2007/0269862 | A1 | 11/2007 | Glass et al. |
| 2011/0053216 | A1 | 3/2011 | Vermaas |

FOREIGN PATENT DOCUMENTS

WO    WO 2011/059745 A1    5/2011

OTHER PUBLICATIONS

Chi, Xiaoyuan, et al., "Comparative analysis of fatty acid desaturases in cyanobacterial genomes," Comparative and Functional Genomics, vol. 2008, Article ID 284508, 25 pages.
Cho, Hyeseon, et al., "Defective export of a periplasmic enzyme disrupts regulation of fatty acid synthesis," J. Biol. Chem., vol. 270, No. 9, pp. 4216-4219 (1995).
D'Andrea, Sabine, et al., "The same rat delta-6-desaturase not only acts on 18- but also on 24-carbon fatty acids in very-long-chain polyunsaturated fatty acid biosynthesis," Biochem. J., vol. 364, pp. 49-55 (2002).
Li, Yuanyou, et al., "Vertebrate fatty acyl desaturase with delta-4 activity," PNAS, vol. 107, No. 39, pp. 16840-16845 (2010).
Liu, Xinyao, et al., "Nickel-inducible lysis system in *Synechocystis* sp. PCC 6803," vol. 106, No. 51, pp. 21550-21554 (2009).
Liu, Xinyao, et al., "Fatty acid production in genetically modified cyanobacteria," PNAS Early Edition, www.pnas.org/cgi/doi/10.1073/pnas.1103014108, pp. 1-6 (2011).
Liu, Xinyao, et al., "CO2-limitation-inducible green recovery of fatty acids from cyanobacterial biomass," PNAS Early Edition, www.pnas.org/cgi/doi/10.1073/pnas.1103016108, pp. 1-4 (2011).
Meyer, Astrid, et al., "Novel fatty acid elongases and their use for the reconstitution of docosahexaenoic acid biosynthesis," Journal of Lipid Research, vol. 45, pp. 1899-1909 (2004).
Sayanova, Olga V., et al., "Eicosapentaenoic acid: biosynthetic routes and the potential for synthesis in transgenic plants," Phytochemistry, vol. 65, pp. 147-158 (2004).
Steen, Eric, J., "Microbial production of fatty-acid-derived fuels and chemicals from plant biomass," Nature, vol. 463, pp. 559-563 (2010).
Takeyama, H., et al., "Expression of the eicosapentaenoic acid synthesis gene cluster from *Shewanella* sp. in a transgenic marine cyanobacterium, *Synechococcus* sp.," Microbiology, vol. 143, pp. 2725-2731 (1997).
Voelker, Toni A., et al., "Alteration of the specificity and regulation of fatty acid synthesis of *Escherichia coli* by expression of a plant medium-chain acyl-acyl carrier protein thioesterase," Journal of Bacteriology, vol. 176, No. 23, pp. 7320-7327(1994).
GenBank Accession No. NC_003272 (Jun. 10, 2013), NCBI Sequence Viewer v2.0, 3 pages, [online] [Retrieved on Sep. 3, 2013] Retrieved from the Internet at <URL:http://www.ncbi.nlm.nih.gov/nuccore/NC_003272>.
GenBank Accession No. NP_489031 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_489031>.
GenBank Accession No. NP_485639 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_485639>.
GenBank Accession No. NC_007413 (Jun. 10, 2013), NCBI Sequence Viewer v2.0, 3 pages, [online] [Retrieved on Sep. 3, 2013] Retrieved from the Internet at <URL:http://www.ncbi.nlm.nih.gov/nuccore/NC_007413>.
GenBank Accession No. YP_322790 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_322790>.
GenBank Accession No. YP_324706 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_324706>.
GenBank Accession No. NZ_AADV02000119 (May 9, 2013), NCBI Sequence Viewer v2.0, 5 pages, [online] [Retrieved on Sep. 3, 2013] Retrieved from the Internet at <URL:http:www.ncbi.nlm.nih.gov/nuccore/NZ_AADV02000119>.

(Continued)

*Primary Examiner* — Maryam Monshipouri
(74) *Attorney, Agent, or Firm* — Fenwick & West LLP

(57) ABSTRACT

Methods of producing an unsaturated free fatty acid comprising at least 18 carbon atoms are provided. In some embodiments, the methods comprise culturing an engineered microorganism in a culture medium, wherein the engineered microorganism comprises at least one recombinant enzyme selected from acyl-lipid desaturase delta-9 (EC:1.14.19.1), acyl-lipid desaturase delta-12 (EC:1.14.19.6), acyl-lipid desaturase delta-15 (EC:1.14.19.-), and thioesterase (EC: 3.1.2.14). Engineered microorganisms comprising at least one of those recombinant enzymes are also provided. The methods and organisms can be used to produce at least one free fatty acid selected from oleic acid, linoleic acid and α-linolenic acid.

21 Claims, 7 Drawing Sheets

(56) References Cited

OTHER PUBLICATIONS

GenBank Accession No. NC_005125 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_005125>.
GenBank Accession No. NP_925812 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_925812>.
GenBank Accession No. NP_924181 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_924181>.
GenBank Accession No. NP_924892 (Jul. 22, 2013), NCBI Sequence Viewer v2.0, 2 pages, [online] [Retrieved on Sep. 4, 2013] Retrieved from the Internet at <URL:http://www.ncbi.nlm.nih.gov/protein/NP_924892>.
GenBank Accession No. NP_924893 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_924893>.
GenBank Accession No. NP_924884 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_924884>.
GenBank Accession No. NP_924886 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_924886>.
GenBank Accession No. NC_008819 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_008819>.
GenBank Accession No. YP_001015962 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001015962>.
GenBank Accession No. NC_007335 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007335>.
GenBank Accession No. YP_292464 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_292464>.
GenBank Accession No. NC_009091 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_009091.
GenBank Accession No. YP_001092086 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001092086>.
GenBank Accession No. NC_008820 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_008820>.
GenBank Accession No. YP_001018890 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001018890>.
GenBank Accession No. YP_001018888 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001018888>.
GenBank Accession No. NC_007577 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007577>.
GenBank Accession No. YP_398261 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_398261>.
GenBank Accession No. NC_005071 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_005071>.
GenBank Accession No. NP_895996 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_895996>.
GenBank Accession No. NP_895998 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_895998>.
GenBank Accession No. NC_008816 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_008816>.
GenBank Accession No. YP_001010271 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001010271>.
GenBank Accession No. NC_008817 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_008817>.
GenBank Accession No. YP_001012176 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001012176>.
GenBank Accession No. NC_005042 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_005042>.
GenBank Accession No. NP_876224 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_876224>.
GenBank Accession No. NC_005072 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_005072>.
GenBank Accession No. NP_893789 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_893789>.
GenBank Accession No. NC_007604 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007604>.
GenBank Accession No. YP_401578 (Jun. 10, 2013), NCBI Sequence Viewer v2.0, 3 pages, [online] [Retrieved on Sep. 3, 2013] Retrieved from the Internet at <URL:http://www.ncbi.nlm.nih.gov/protein/YP_401578>.
GenBank Accession No. NC_006576 (Aug. 27, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_006576>.
GenBank Accession No. YP_172259 (Aug. 27, 2013), NCBI Sequence Viewer v2.0, 3 pages, [online] [Retrieved on Sep. 3, 2013] Retrieved from the Internet at <URL:http://www.ncbi.nlm.nih.gov/protein/YP_172259>.
GenBank Accession No. NC_008319 (Jun. 10, 2013), NCBI Sequence Viewer v2.0, 2 pages, [online] [Retrieved on Sep. 3, 2013] Retrieved from the Internet at URL:http://www.ncbi.nlm.nih.gov/nuccore/NC_008319
GenBank Accession No. YP_731981 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_731981>.

(56) References Cited

OTHER PUBLICATIONS

GenBank Accession No. YP_731979 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_731979>.
GenBank Accession No. NC_007516 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007516>.
GenBank Accession No. YP_382824 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_382824>.
GenBank Accession No. NC_007513 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007513>.
GenBank Accession No. YP_378192 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_378192>.
GenBank Accession No. YP_378193 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_378193>.
GenBank Accession No. NC_007776 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007776>.
GenBank Accession No. YP_477105 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_477105>.
GenBank Accession No. NC_007775 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_007775>.
GenBank Accession No. YP_475739 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_475739>.
GenBank Accession No. NC_009482 (Aug. 27, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_009482>.
GenBank Accession No. YP_001228651 (Aug. 27, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001228651>.
GenBank Accession No. YP_001228649 (Aug. 27, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001228649>.
GenBank Accession No. NC_009481 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_009481>.
GenBank Accession No. YP_001226140 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001226140>.
GenBank Accession No. YP_001226138 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001226138>.
GenBank Accession No. NC_005070 (May 23, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_005070>.
GenBank Accession No. NP_898466 (May 23, 2013), NCBI Sequence Viewer v2.0, 2 pages, [online] [Retrieved on Sep. 3, 2013] Retrieved from the Internet at <URL:http://www.ncbi.nlm.nih.gov/protein/NP_898466>.
GenBank Accession No. NC_000911 (Jun. 27, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_000911>.
GenBank Accession No. NP_442430 (Jun. 27, 2013), NCBI Sequence Viewer v2.0, 3 pages, [online] [Retrieved on Sep. 3, 2013] Retrieved from the Internet at <URL:http://www.ncbi.nlm.nih.gov/protein/NP_442430>.
GenBank Accession No. NC_004113 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/nuccore/NC_004113>.
GenBank Accession No. NP_682509 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_682509>.
GenBank Accession No. NP_683170 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_683170>.
GenBank Accession No. NP_682443 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_682443>.
GenBank Accession No. NC_008312 (Jun. 10, 2013), NCBI Sequence Viewer v2.0, 3 pages, [online] [Retrieved on Sep. 3, 2013] Retrieved from the Internet at <URL:http://www.ncbi.nlm.nih.gov/nuccore/NC_008312>.
GenBank Accession No. YP_721205 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_721205>.
GenBank Accession No. NZ_AAVW01000082 (May 8, 2013), NCBI Sequence Viewer v2.0, 7 pages, [online] [Retrieved on Sep. 3, 2013] Retrieved from the Internet at <URL:http://www.ncbi.nlm.nih.gov/nuccore/NZ_AAVW01000082>.
GenBank Accession No. NZ_AAVW01000142 (May 8, 2013), NCBI Sequence Viewer v2.0, 3 pages, [online] [Retrieved on Sep. 3, 2013] Retrieved from the Internet at <URL:http://www.ncbi.nlm.nih.gov/nuccore/NZ_AAVW01000142>.
GenBank Accession No. NZ_AAXW01000001 (May 10, 2013), NCBI Sequence Viewer v2.0, 54 pages, [online] [Retrieved on Sep. 3, 2013] Retrieved from the Internet at <URL:http://www.ncbi.nlm.nih.gov/nuccore/NZ_AAXW01000001>.
GenBank Accession No. NZ_AAXW01000014 (May 10, 2013), NCBI Sequence Viewer v2.0, 34 pages, [online] [Retrieved on Sep. 3, 2013] Retrieved from the Internet at <URL:http://www.ncbi.nlm.nih.gov/nuccore/NZ_AAXW01000014>.
GenBank Accession No. NP_485638 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_485638>.
GenBank Accession No. YP_324705 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_324705>.
GenBank Accession No. NZ_AADV02000040 (May 9, 2013), NCBI Sequence Viewer v2.0, 7 pages, [online] [Retrieved on Sep. 3, 2013] Retrieved from the Internet at <URL:http://www.ncbi.nlm.nih.gov/nuccore/NZ_AADV02000040>.
GenBank Accession No. NZ_AADV02000003 (May 9, 2013), NCBI Sequence Viewer v2.0, 78 pages, [online] [Retrieved on Sep. 3, 2013] Retrieved from the Internet at <URL:http://www.ncbi.nlm.nih.gov/nuccore/NZ_AADV02000003>.
GenBank Accession No. NP_925569 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_925569>.

(56) References Cited

OTHER PUBLICATIONS

GenBank Accession No. NP_926681 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_926681>.
GenBank Accession No. YP_001014905 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001014905>.
GenBank Accession No. YP_291588 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_291588>.
GenBank Accession No. YP_001091800 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001091800>.
GenBank Accession No. YP_001091796 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001091796>.
GenBank Accession No. YP_001017424 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001017424>.
GenBank Accession No. YP_001018108 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001018108>.
GenBank Accession No. YP_397972 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_397972>.
GenBank Accession No. YP_397969 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_397969>.
GenBank Accession No. NP_894082 (Jun. 10, 2013), NCBI Sequence Viewer v2.0, 2 pages [online] [Retrieved on Sep. 3, 2013] Retrieved from the Internet at <URL:http://www.ncbi.nlm.nih.gov/protein/NP_894082>.
GenBank Accession No. NP_894629 (Jun. 10, 2013) NCBI Sequence Viewer v2.0, 2 pages, [online] [Retrieved on Sep. 3, 2013] Retrieved from the Internet at <URL:http://www.ncbi.nlm.nih.gov/protein/NP_894629>.
GenBank Accession No. YP_001009982 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001009982>.
GenBank Accession No. YP_001009977 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001009977>.
GenBank Accession No. YP_001011874 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001011874>.
GenBank Accession No. YP_001011866 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_001011866>.
GenBank Accession No. NP_875600 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_875600>.
GenBank Accession No. NP_875606 (Jul. 22, 2013), NCBI Sequence Viewer v2.0, 2 pages, [online] [Retrieved on Sep. 3, 2013] Retrieved from the Internet at <URL:http://www.ncbi.nlm.nih.gov/protein/NP_875606>.
GenBank Accession No. NP_893499 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_893499>.
GenBank Accession No. NP_893495 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/NP_893495>.
GenBank Accession No. YP_729627 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_729627>.
GenBank Accession No. YP_382268 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_382268>.
GenBank Accession No. YP_376159 (Jun. 10, 2013), NCBI Sequence Viewer v2.0, 2 pages, [online] [Retrieved on Sep. 3, 2013] Retrieved from the Internet at <URL:http://www.ncbi.nlm.nih.gov/protein/YP_376159>.
GenBank Accession No. YP_001228013 (Aug. 27, 2013), NCBI Sequence Viewer v2.0, 2 pages, [online] [Retrieved on Sep. 4, 2013] Retrieved from the Internet at <URL:http://www.ncbi.nlm.nih.gov/protein/YP_001228013>.
GenBank Accession No. NC_009481 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/nuccore/NC_009481>.
GenBank Accession No. YP_001224312 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/protein/YP_001224312>.
GenBank Accession No. NC_005070 (May 23, 2013), NCBI Sequence Viewer v2.0, 2 pages, [online] [Retrieved on Sep. 4, 2013] Retrieved from the Internet at <URL:http://www.ncbi.nlm.nih.gov/nuccore/NC_005070>.
GenBank Accession No. NP_896789 (May 23, 2013), NCBI Sequence Viewer v2.0, 2 pages, [online] [Retrieved on Sep. 4, 2013] Retrieved from the Internet at <URL:http://www.ncbi.nlm.nih.gov/protein/NP_896789>.
GenBank Accession No. NP_897787 (May 23, 2013), NCBI Sequence Viewer v2.0, 2 pages, [online] [Retrieved on Sep. 4, 2013] Retrieved from the Internet at <URL:http://www.ncbi.nlm.nih.gov/protein/NP_897787>.
GenBank Accession No. NC_000911 (Jun. 27, 2013), NCBI Sequence Viewer v2.0, 2 pages, [online] [Retrieved on Sep. 4, 2013] Retrieved from the Internet at <URL:http://www.ncbi.nlm.nih.gov/nuccore/NC_000911>.
GenBank Accession No. NP_441489 (Jun. 27, 2013), NCBI Sequence Viewer v2.0, 3 pages, [online] [Retrieved on Sep. 4, 2013] Retrieved from the Internet at <URL:http://www.ncbi.nlm.nih.gov/protein/NP_441489>.
GenBank Accession No. NC_008312 (Jun. 10, 2013), NCBI Sequence Viewer v2.0, 3 pages, [online] [Retrieved on Sep. 4, 2013] Retrieved from the Internet at <URL:http://www.ncbi.nlm.nih.gov/nuccore/NC_008312>.
GenBank Accession No. YP_720110 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/protein/YP_720110>.
GenBank Accession No. NZ_AAVU01000015 (May 11, 2013), NCBI Sequence Viewer v2.0, 29 pages, [online] [Retrieved on Sep. 4, 2013] Retrieved from the Internet at <URL:http://www.ncbi.nlm.nih.gov/nuccore/NZ_AAVU01000015>.
GenBank Accession No. NZ_AAVW01000142 (May 8, 2013), NCBI Sequence Viewer v2.0, 3 pages, [online] [Retrieved on Sep. 4, 2013] Retrieved from the Internet at <URL:http://www.ncbi.nlm.nih.gov/nuccore/NZ_AAVW01000142>.
GenBank Accession No. NZ_AAXW01000104 (May 10, 2013), NCBI Sequence Viewer v2.0, 4 pages, [online] [Retrieved on Sep. 4, 2013] Retrieved from the Internet at <URL:http://www.ncbi.nlm.nih.gov/nuccore/NZ_AAXW01000104>.

(56) References Cited

OTHER PUBLICATIONS

GenBank Accession No. NP_485637 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/protein/NP_485637>.
GenBank Accession No. NC_007413 (Jun. 10, 2013), NCBI Sequence Viewer v2.0, 3 pages, [online] [Retrieved on Sep. 4, 2013] Retrieved from the Internet at <URL:http://www.ncbi.nlm.nih.gov/nuccore/NC_007413>.
GenBank Accession No. YP_24704 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/protein/YP_324704>.
GenBank Accession No. NZ_AADV02000017 (May 9, 2013), NCBI Sequence Viewer v2.0, 9 pages, [online] [Retrieved on Sep. 4, 2013] Retrieved from the Internet at <URL:http://www.ncbi.nlm.nih.gov/nuccore/NZ_AADV02000017>.
GenBank Accession No. YP_001225348 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/protein/YP_001225348>.
GenBank Accession No. NP_441622 (Jun. 27, 2013), NCBI Sequence Viewer v2.0, 3 pages, [online] [Retrieved on Sep. 4, 2013] Retrieved from the Internet at <URL:http://www.ncbi.nlm.nih.gov/protein/NP_441622>.
GenBank Accession No. YP_723951 (Jun. 10, 2013), NCBI Sequence Viewer v2.0, 2 pages, [online] [Retrieved on Sep. 4, 2013] Retrieved from the Internet at <URL:http://www.ncbi.nlm.nih.gov/protein/YP_723951>.
GenBank Accession No. NZ_AAVU01000077 (May 11, 2013), NCBI Sequence Viewer v2.0, 5 pages, [online] [Retrieved on Sep. 4, 2013] Retrieved from the Internet at <URL:http://www.ncbi.nlm.nih.gov/nuccore/NZ_AAVU01000077>.
GenBank Accession No. NZ_AAXW01000009 (May 10, 2013), NCBI Sequence Viewer v2.0, 31 pages, [online] [Retrieved on Sep. 4, 2013] Retrieved from the Internet at <URL:http://www.ncbi.nlm.nih.gov/nuccore/NZ_AAXW01000009>.
GenBank Accession No. NM_113415 (Jun. 5, 2013), NCBI Sequence Viewer v2.0, 3 pages, [online] [Retrieved on Sep. 4, 2013] Retrieved from the Internet at <URL:http://www.ncbi.nlm.nih.gov/nuccore/NM_113415>.
GenBank Accession No. NP_189147 (Jun. 5, 2013), NCBI Sequence Viewer v2.0, 3 pages, [online] [Retrieved on Sep. 4, 2013] Retrieved from the Internet at <URL:http://www.ncbi.nlm.nih.gov/protein/NP_189147>.
GenBank Accession No. AJ278479 (Nov. 14, 2006), NCBI Sequence Viewer v2.0, 2 pages, [online] [Retrieved on Sep. 4, 2013] Retrieved from the Internet at <URL:http://www.ncbi.nlm.nih.gov/nuccore/AJ278479>.
GenBank Accession No. CAC14164 (Nov. 14, 2006), NCBI Sequence Viewer v2.0, 2 pages, [online] [Retrieved on Sep. 4, 2013] Retrieved from the Internet at <URL:http://www.ncbi.nlm.nih.gov/protein/CAC14164>.
GenBank Accession No. L06182 (Aug. 11, 2008), NCBI Sequence Viewer v2.0, 2 pages, [online] [Retrieved on Sep. 4, 2013] Retrieved from the Internet at <URL:http://www.ncbi.nlm.nih.gov/nuccore/L06182>.
GenBank Accession No. AAA24664 (Aug. 11, 2008), NCBI Sequence Viewer v2.0, 2 pages, [online] [Retrieved on Sep. 4, 2013] Retrieved from the Internet at <URL:http://www.ncbi.nlm.nih.gov/protein/AAA24664>.
Allen EE, Bartlett DH. Structure and regulation of the omega-3 polyunsaturated fatty acid synthase genes from the deep-sea bacterium *Photobacterium profundum* strain SS9. Microbiology 2002;148:1903-13.
Allen EE, Facciotti D, Bartlett DH. Monounsaturated but Not Polyunsaturated Fatty Acids are Required for Growth of the Deep-Sea Bacterium *Photobacterium profundum* SS9 at High Pressure and Low Temperature. Appl Environ Microbiol 1999;65:1710.

Christian, B, Lichti B, Pulz O, Grewe C, Luckas B. Fast and unambiguous determination of EPA and DHA content in oil of selected strains of algae and cyanobacteria. Acta Agron Hungarica 2009;57:249-53.
De Swaaf, ME, de Rijk TC, van der Meer P, Eggink G, Sijtsma L. Analysis of docosahexaenoic acid biosynthesis in *Crypthecodinium cohnii* by 13C labelling and desaturase inhibitor experiments. J Biotechnol 2003;103:21-9.
Gratraud, P, Huws E, Falkard B, Adjalley S, Fidock D a, Berry L, et al. Oleic acid biosynthesis in *Plasmodium falciparum*: characterization of the stearoyl-CoA desaturase and investigation as a potential therapeutic target. PLoS One 2009;4:e6889.
Kautharapu, KB, Rathmacher J, Jarboe LR. Growth condition optimization for docosahexaenoic acid (DHA) production by Moritella marina MP-1. Appl Microbiol Biotechnol 2012.
Liu, X, Brune D, Vermaas W, Curtiss R. Production and secretion of fatty acids in genetically engineered cyanobacteria. Proc Natl Acad Sci U S A 2010;6803.
Lu, X, Vora H, Khosla C. Overproduction of free fatty acids in *E. coli*: implications for biodiesel production. Metab Eng 2008;10:333-9.
Okuyama, H, Orikasa Y, Nishida T, Watanabe K, Morita N. Bacterial genes responsible for the biosynthesis of eicosapentaenoic and docosahexaenoic acids and their heterologous expression. Appl Enivironmental Microbiol 2007;73:665-70.
Orikasa, Y, Nishida T, Yamada A, Yu R, Watanabe K, Hase A, et al. Recombinant production of docosahexaenoic acid in a polyketide biosynthesis mode in *Escherichia coli*. Biotechnol Lett 2006;28:1841-7.
Sakamoto, T, Bryant D. Temperature-regulated mRNA accumulation and stabilization for fatty acid desaturase genes in the cyanobacterium *Synechococcus* sp. strain PCC 7002. Mol Microbiol 1997;23:1281-92.
Sakamoto, T, Los D, Higashi S, Wada H, Nishida I, Ohmori M, et al. Cloning of omega 3 desaturase from cyanobacteria and its use in altering the degree of membrane-lipid unsaturation. Plant Mol Biol 1994;26:249-63.
Sakamoto, T, Shen G, Higashi S, Murata N, Bryant D a. Alteration of low-temperature susceptibility of the cyanobacterium *Synechococcus* sp. PCC 7002 by genetic manipulation of membrane lipid unsaturation. Arch Microbiol 1998;169:20-8.
Tanaka, M, Ueno A, Kawasaki K, Yumoto I, Ohgiya S, Ishizaki K, et al. Isolation of clustered genes that are notably homologous to the eicosapentaenoic acid biosynthesis gene cluster from the docosahexaenoic acid-producing bacterium *Vibrio marinus* strain MP-1. Biotechnol Lett 1999;1:939-45.
Voss, A, Reinhart M, Sankarappa S, Sprechers H. The Metabolism of 7,10,13,16,19-Docosapentaenoic Acid to 4,7,10,13,16,10-Docosahexaenoic Acid in Rat Liver is Independent of a 4-Desaturase. J Biol Chem 1991;266:19995-20000.
GenBank Accession No. ZP_00518170 (Nov. 9, 2010), NCBI Sequence Viewer v2.0, 2 pages, [online] [Retrieved on Mar. 28, 2014] Retrieved from the Internet at <URL:http://www.ncbi.nlm.nih.gov/protein/ZP_00518170.1?report=genpept>.
GenBank Accession No. NZ_AAAY02000002 (Oct. 1, 2004), NCBI Sequence Viewer v2.0, 96 pages, [online] [Retrieved on Mar. 28, 2014] Retrieved from the Internet at <URL: http://www.ncbi.nlm.nih.gov/nuccore/NZ_AAAY02000002.1?report=genbank>.
GenBank Accession No. ZP_00345918 (Oct. 1, 2004), NCBI Sequence Viewer v2.0, 2 pages, [online] [Retrieved on Mar. 28, 2014] Retrieved from the Internet at <URL: http://www.ncbi.nlm.nih.gov/protein/ZP_00345918.1?report=genpept>.
GenBank Accession No. NZ_AAAY02000046 (Oct. 1, 2004), NCBI Sequence Viewer v2.0, 30 pages, [online] [Retrieved on Mar. 28, 2014] Retrieved from the Internet at <URL: http://www.ncbi.nlm.nih.gov/nuccore/NZ_AAAY02000046.1?report=genbank>.
GenBank Accession No. ZP_00108582 (Oct. 1, 2004), NCBI Sequence Viewer v2.0, 2 pages, [online] [Retrieved on Mar. 28, 2014] Retrieved from the Internet at <URL: http://www.ncbi.nlm.nih.gov/protein/ZP_00108582.1?report=genpept>.
GenBank Accession No. NZ_AALP01000001 (Jan. 6, 2006), NCBI Sequence Viewer v2.0, 281 pages, [online] [Retrieved on Mar. 28, 2014] Retrieved from the Internet at <URL: http://www.ncbi.nlm.nih.gov/nuccore/NZ_AALP01000001.1?report=genbank>.

(56) References Cited

OTHER PUBLICATIONS

GenBank Accession No. ZP_01006363 (Jan. 6, 2006), NCBI Sequence Viewer v2.0, 2 pages, [online] [Retrieved on Mar. 28, 2014] Retrieved from the Internet at <URL: http://www.ncbi.nlm.nih.gov/protein/ZP_01006363.1?report=genpept>.
GenBank Accession No. NZ_AATZ01000002 (Nov. 14, 2014), NCBI Sequence Viewer v2.0, 2 pages, [online] [Retrieved on Mar. 28, 2014] Retrieved from the Internet at <URL: http://www.ncbi.nlm.nih.gov/nuccore/NZ_AATZ01000002.1?report=genbank>.
GenBank Accession No. ZP_01469203 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01469203.1?report=genpept>.
GenBank Accession No. ZP_01469204 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01469204.1?report=genpept>.
GenBank Accession No. NZ_AAUA01000001 (Nov. 14, 2012), NCBI Sequence Viewer v2.0, 2 pages, [online] [Retrieved on Mar. 28, 2014] Retrieved from the Internet at <URL: http://www.ncbi.nlm.nih.gov/nuccore/NZ_AAUA01000001.1?report=genbank>.
GenBank Accession No. ZP_01471384 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01471384.1?report=genpept>.
GenBank Accession No. ZP_01471382 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01471382.1?report=genpept>.
GenBank Accession No. ZP_01079314 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01079314.1?report=genpept>.
GenBank Accession No. ZP_01079312 (Nov. 26, 2012), NCBI Sequence Viewer v2.0, 5 pages, [online] [Retrieved on Mar. 28, 2014] Retrieved from the Internet at <URL: http://www.ncbi.nlm.nih.gov/protein/ZP_01079312.1?report=genpept>.
GenBank Accession No. NZ_AANO01000004 (Nov. 14, 2012), NCBI Sequence Viewer v2.0, 2 pages, [online] [Retrieved on Mar. 28, 2014] Retrieved from the Internet at <URL:http://www.ncbi.nlm.nih.gov/nuccore/NZ_AANO01000004.1?report=genbank>.
GenBank Accession No. ZP_01084898 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01084898.1?report=genpept>.
GenBank Accession No. ZP_01084896 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01084896.1?report=genpept>.
GenBank Accession No. NZ_AAOK01000005 (Nov. 14, 2012), NCBI Sequence Viewer v2.0, 2 pages, [online] [Retrieved on Mar. 28, 2014] Retrieved from the Internet at <URL: http://www.ncbi.nlm.nih.gov/nuccore/NZ_AAOK01000005.1?report=genbank>.
GenBank Accession No. ZP_01125021 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01125021.1?report=genpept>.
GenBank Accession No. ZP_01125023 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01125023.1?report=genpept>.
GenBank Accession No. NZ_AAVU01000086 (May 11, 2013), NCBI Sequence Viewer v2.0, 3 pages., [online] [Retrieved on Mar. 28, 2014] Retrieved from the Internet at <URL: http://www.ncbi.nlm.nih.gov/nuccore/NZ_AAVU01000086>.
GenBank Accession No. ZP_01624678 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01624678.1?report=genpept>.
GenBank Accession No. ZP_01631817 (Nov. 9, 2010), NCBI Sequence Viewer v2.0, 2 pages, [online] [Retrieved on Mar. 28, 2014] Retrieved from the Internet at <URL:http://www.ncbi.nlm.nih.gov/protein/ZP_01631817.1?report=genpept>.
GenBank Accession No. ZP_01632615 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01632615.1?report=genpept>.
GenBank Accession No. ZP_01726409 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01726409.1?report=genpept>.
GenBank Accession No. ZP_01729213 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01729213.1?report=genpept>.
GenBank Accession No. ZP_00516843 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_00516843.1?report=genpept>.
GenBank Accession No. ZP_00515010 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_00515010.1?report=genpept>.
GenBank Accession No. ZP_00108583 (Oct. 1, 2004), NCBI Sequence Viewer v2.0, 2 pages, [online] [Retrieved on Mar. 28, 2014] Retrieved from the Internet at <URL: http://www.ncbi.nlm.nih.gov/protein/ZP_00108583.2?report=genpept>.
GenBank Accession No. ZP_01005647 (Jan. 6, 2006), NCBI Sequence Viewer v2.0, 2 pages, [online] [Retrieved on Mar. 28, 2014] Retrieved from the Internet at <URL:http://www.ncbi.nlm.nih.gov/protein/ZP_01005647.1?report=genpept>.
GenBank Accession No. ZP_01005648 (Jan. 6, 2006), NCBI Sequence Viewer v2.0, 2 pages, [online] [Retrieved on Mar. 28, 2014] Retrieved from the Internet at <URL: http://www.ncbi.nlm.nih.gov/protein/ZP_01005648.1?report=genpept>.
GenBank Accession No. ZP_01468963 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01468963.1?report=genpept>.
GenBank Accession No. NZ_AANP01000005 (Nov. 14, 2012), NCBI Sequence Viewer v2.0, 5 pages, [online] [Retrieved on Mar. 28, 2014] Retrieved from the Internet at <URL: http://www.ncbi.nlm.nih.gov/nuccore/NZ_AANP01000005.1?report=genbank>.
GenBank Accession No. ZP_01080849 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01080849.1?report=genpept>.
GenBank Accession No. NZ_AANO01000002 (Nov. 14, 2012), NCBI Sequence Viewer v2.0, 2 pages, [online] [Retrieved on Mar. 28, 2014] Retrieved from the Internet at <URL: http://www.ncbi.nlm.nih.gov/nuccore/NZ_AANO01000002.1?report=genbank>.
GenBank Accession No. ZP_01083974 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01083974.1?report=genpept>.
GenBank Accession No. NZ_AANO01000079 (May 8, 2013), NCBI Sequence Viewer v2.0, 2 pages, [online] [Retrieved on Mar. 28, 2014] Retrieved from the Internet at <URL: http://www.ncbi.nlm.nih.gov/nuccore/NZ_AANO01000079>.
GenBank Accession No. ZP_01086617 (Nov. 10, 2010), NCBI Sequence Viewer v2.0, 2 pages, [online] [Retrieved on Mar. 28, 2014] Retrieved from the Internet at <URL:http://www.ncbi.nlm.nih.gov/protein/ZP_01086617.1?report=genpept>.
GenBank Accession No. NZ_AAOK01000004 (Nov. 14, 2012), NCBI Sequence Viewer v2.0, 2 pages, [online] [Retrieved on Mar. 28, 2014] Retrieved from the Internet at <URL: http://www.ncbi.nlm.nih.gov/nuccore/NZ_AAOK01000004.1?report=genbank>.
GenBank Accession No. ZP_01124768 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01124768.1?report=genpept>.

(56) References Cited

OTHER PUBLICATIONS

GenBank Accession No. ZP_01124517 (Nov. 26, 2012), NCBI Sequence Viewer v2.0, 2 pages, [online] [Retrieved on Mar. 28, 2014] Retrieved from the Internet at <URL: http://www.ncbi.nlm.nih.gov/protein/ZP_01124517.1?report=genpept>.

GenBank Accession No. ZP_01621185 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01621185.1?report=genpept>.

GenBank Accession No. ZP_01632616 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01632616.1?report=genpept>.

GenBank Accession No. ZP_01732458 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01732458.1?report=genpept>.

GenBank Accession No. ZP_00516181 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_00516181.1?report=genpept>.

GenBank Accession No. ZP_00108584 (Oct. 1, 2004), NCBI Sequence Viewer v2.0, 2 pages, [online] [Retrieved on Mar. 28, 2014] Retrieved from the Internet at <URL: http://www.ncbi.nlm.nih.gov/protein/ZP_00108584.1?report=genpept>.

GenBank Accession No. ZP_01624560 (Nov. 9, 2010), NCBI Sequence Viewer v2.0, 4 pages, [online] [Retrieved on Mar. 28, 2014] Retrieved from the Internet at <URL: http://www.ncbi.nlm.nih.gov/protein/ZP_01624560.1?report=genpept>.

GenBank Accession No. ZP_01632617 (Nov. 9, 2010), NCBI Sequence Viewer v2.0, 2 pages, [online] [Retrieved on Mar. 28, 2014] Retrieved from the Internet at <URL: http://www.ncbi.nlm.nih.gov/protein/ZP_01632617.1?report=genpept>.

GenBank Accession No. ZP_01728541 (Nov. 9, 2010), NCBI Sequence Viewer v2.0, 5 pages, [online] [Retrieved on Mar. 28, 2014] Retrieved from the Internet at <URL: http://www.ncbi.nlm.nih.gov/protein/ZP_01728541.1?report=genpept>.

GenBank Accession No. NP_441489 (Mar. 19, 2014), NCBI Sequence Viewer v2.0, 2 pages, [online] [Retrieved on Mar. 28, 2014] Retrieved from the Internet at <URL: http://www.ncbi.nlm.nih.gov/protein/NP_441489>.

MICROORGANISMS AND METHODS FOR PRODUCING UNSATURATED FATTY ACIDS

SEQUENCE LISTING

The instant application contains a Sequence Listing which has been submitted in ASCII format via EFS-Web and is hereby incorporated by reference in its entirety. Said ASCII copy, created on Dec. 13, 2011, is named 100501US.txt and is 9,090 bytes in size.

INTRODUCTION

Foods, fuels and chemicals have been produced from the fatty acids of plant and animal oils for centuries. Many nutritional oils include unsaturated fatty acids. In humans, two such unsaturated fatty acids, linoleic acid (18:2) and α-linolenic acid (18:3), are essential fatty acids, i.e., fatty acids that are essential for good heath but must be ingested in the diet because they are not synthesized in the body. The positive effects of certain unsaturated fatty acids on cardiovascular, neurological and immune system health are well-documented. In addition, unsaturated fatty acids are the raw materials for a growing diversity of products including surfactants, solvents, lubricants and waxes. In some cases, the increased demand of these unsaturated fatty acids has resulted in higher prices, questionable land-use practices, and environmental concerns associated with their production. A sustainable alternative to produce unsaturated free fatty acids would therefore be useful. This disclosure provides engineered microorganisms and methods of using them to make at least one unsaturated free fatty acid.

In particular, methods of producing an unsaturated free fatty acid comprising at least 18 carbon atoms are provided. In some embodiments the method comprise culturing an engineered microorganism in a culture medium, wherein the engineered microorganism comprises at least one recombinant enzyme selected from acyl-lipid desaturase delta-9 (EC:1.14.19.1), acyl-lipid desaturase delta-12 (EC:1.14.19.6), acyl-lipid desaturase delta-15 (EC:1.14.19.-) and thioesterase (EC:3.1.2.14). Engineered microorganisms comprising at least one of those recombinant enzymes are also provided. The methods and organisms can be used to produce at least one free fatty acid selected from oleic acid, linoleic acid, and α-linolenic acid, for example.

SUMMARY

Provided herein are methods for producing an unsaturated free fatty acid comprising at least 18 carbon atoms. In some embodiments, the methods comprise culturing an engineered microorganism in a culture medium, wherein the engineered microorganism comprises at least one recombinant acyl-lipid desaturase specific for a substrate comprising at least 18 carbon atoms. In some embodiments of the methods, the amount of the unsaturated free fatty acid comprising at least 18 carbon atoms produced by the engineered microorganism is increased relative to the amount of the unsaturated free fatty acid comprising at least 18 carbon atoms produced by an otherwise identical microorganism lacking the at least one recombinant acyl-lipid desaturase. In some embodiments of the methods, the at least one recombinant acyl-lipid desaturase is selected from acyl-lipid desaturase delta-9 (EC: 1.14.19.1), acyl-lipid desaturase delta-12 (EC:1.14.19.6), and acyl-lipid desaturase delta-15 (EC:1.14.19.-). In some embodiments of the methods, the unsaturated free fatty acid comprising at least 18 carbon atoms is selected from oleic acid, linoleic acid and α-linolenic acid. In some embodiments of the methods, production of at least one of oleic acid, linoleic acid, and α-linolenic acid is increased in the engineered microorganism relative to production of at least one of the corresponding oleic acid, linoleic acid and α-linolenic acid produced by an otherwise identical microorganism lacking the recombinant acyl-lipid desaturase.

In some embodiments of the methods, the at least one recombinant acyl-lipid desaturase is a recombinant acyl-lipid desaturase delta-9 (EC:1.14.19.1). In some embodiments, the engineered microorganism produces oleic acid, and the production of oleic acid is increased in the engineered microorganism relative to production of oleic acid by an otherwise identical microorganism lacking the recombinant acyl-lipid desaturase delta-9 (EC:1.14.19.1).

In some embodiments of the methods, the engineered microorganism comprises a recombinant acyl-lipid desaturase delta-12 (EC:1.14.19.6). In some embodiments, the engineered microorganism produces linoleic acid, and the production of linoleic acid is increased in the engineered microorganism relative to production of linoleic acid by an otherwise identical microorganism lacking the recombinant acyl-lipid desaturase delta-12 (EC:1.14.19.6).

In some embodiments of the methods, the engineered microorganism comprises a recombinant acyl-lipid desaturase delta-15 (EC:1.14.19.-). In some embodiments, the engineered microorganism produces α-linolenic acid, and the production of α-linolenic acid is increased in the engineered microorganism relative to production of α-linolenic acid by an otherwise identical microorganism lacking the recombinant acyl-lipid desaturase delta-15 (EC:1.14.19.-).

In some embodiments of the methods, the engineered microorganism comprises a recombinant acyl-lipid desaturase delta-12 (EC:1.14.19.6) and a recombinant acyl-lipid desaturase delta-15 (EC:1.14.19.-). In some embodiments, the engineered microorganism produces α-linolenic acid, and the production of α-linolenic acid is increased in the engineered microorganism relative to production of α-linolenic acid by an otherwise identical microorganism lacking at least one of the recombinant acyl-lipid desaturase delta-12 (EC: 1.14.19.6) and the recombinant acyl-lipid desaturase delta-15 (EC:1.14.19.-). In some embodiments, the engineered microorganism further comprises a recombinant acyl-lipid desaturase delta-9 (EC:1.14.19.1). In some embodiments, the production of α-linolenic acid is increased in the engineered microorganism relative to production of α-linolenic acid by an otherwise identical microorganism lacking at least one of the recombinant acyl-lipid desaturase delta-9 (EC:1.14.19.1), the recombinant acyl-lipid desaturase delta-12 (EC: 1.14.19.6) and the recombinant acyl-lipid desaturase delta-15 (EC:1.14.19.-).

In some embodiments of the methods, the engineered microorganism comprises a recombinant acyl-lipid desaturase delta-9 (EC:1.14.19.1), a recombinant acyl-lipid desaturase delta-12 (EC:1.14.19.6) and a recombinant acyl-lipid desaturase delta-15 (EC:1.14.19.-). In some embodiments, the engineered microorganism produces oleic acid, linoleic acid and α-linolenic acid, and the production of at least one of oleic acid, linoleic acid and α-linolenic acid is increased in the engineered microorganism relative to the production of the corresponding oleic acid, linoleic acid and α-linolenic acid by an otherwise identical microorganism lacking at least one of the recombinant acyl-lipid desaturase delta-9 (EC: 1.14.19.1), the recombinant acyl-lipid desaturase delta-12 (EC:1.14.19.6) and the recombinant acyl-lipid desaturase delta-15 (EC:1.14.19.-).

In some embodiments of the methods, the amount of the unsaturated free fatty acid comprising at least 18 carbon atoms produced by the engineered microorganism is increased by at least 100% relative to the amount of the unsaturated free fatty acid comprising at least 18 carbon atoms produced by an otherwise identical microorganism lacking the at least one recombinant acyl-lipid desaturase.

In some embodiments of the methods, the amount of the unsaturated free fatty acid selected from oleic acid, linoleic acid and α-linolenic acid produced by the engineered microorganism is increased by at least 100% relative to the amount of the unsaturated free fatty acid selected from oleic acid, linoleic acid and α-linolenic acid produced by an otherwise identical microorganism lacking the at least one recombinant acyl-lipid desaturase selected from acyl-lipid desaturase delta-9 (EC:1.14.19.1), acyl-lipid desaturase delta-12 (EC: 1.14.19.6), and acyl-lipid desaturase delta-15 (EC:1.14.19.-).

In some embodiments of the methods, the amount of at least one free fatty acid selected from oleic acid, linoleic acid, and α-linolenic acid is increased by at least 100% relative to the amount of the unsaturated free fatty acid selected from oleic acid, linoleic acid, and α-linolenic acid produced by an otherwise identical microorganism lacking the recombinant acyl-lipid desaturase delta-9 (EC:1.14.19.1), recombinant acyl-lipid desaturase delta-12 (EC:1.14.19.6) and recombinant acyl-lipid desaturase delta-15 (EC:1.14.19.-).

In some embodiments of the methods, the engineered microorganism comprises recombinant subunits accB, accC, accD, and accA of the acetyl-CoA carboxylase enzyme (EC: 6.4.1.2).

In some embodiments of the methods, production of at least one protein selected from phosphoenolpyruvate carboxylase (EC 4.1.1.31), NADtdependent D-lactate dehydrogenase (EC 1.1.1.28), 2-isopropylmalate synthase (EC 2.3.3.13), citrate (Si)-synthase (EC 2.3.3.1), acetyl-CoA C-acetyltransferase (EC 2.3.1.9), phosphate acetyltransferase (EC 2.3.1.8), and acetate kinase (EC 2.7.2.1) is reduced or eliminated in the engineered microorganism.

In some embodiments of the methods, production of acyl-ACP synthetase (EC:6.2.1.20) is reduced or eliminated in the engineered microorganism.

In some embodiments of the methods, the engineered microorganism further comprises a recombinant thioesterase (EC:3.1.2.14). In some embodiments, the recombinant thioesterase (EC:3.1.2.14) is localized to the cytosol. In some embodiments, the unsaturated free fatty acid comprising at least 18 carbon atoms produced by the engineered microorganism is secreted into the culture medium in an amount that is greater than the amount of the unsaturated free fatty acid comprising at least 18 carbon atoms secreted into the culture medium by an otherwise identical microorganism lacking the recombinant thioesterase (EC:3.1.2.14). In some embodiments of the methods, at least one polar cell layer of the engineered microorganism comprises a modification that increases free fatty acid secretion into the cell culture medium.

In some embodiments, the at least one recombinant acyl-lipid desaturase is selected from acyl-lipid desaturase delta-9 (EC:1.14.19.1), acyl-lipid desaturase delta-12 (EC: 1.14.19.6), and acyl-lipid desaturase delta-15 (EC:1.14.19.-). In some embodiments, the unsaturated free fatty acid comprising at least 18 carbon atoms is selected from oleic acid, linoleic acid and α-linolenic acid, and production and secretion into the culture medium of at least one of oleic acid, linoleic acid, and α-linolenic acid is increased in the engineered microorganism relative to production and secretion into the culture medium of the corresponding oleic acid, linoleic acid and α-linolenic acid produced by an otherwise identical microorganism lacking the recombinant acyl-lipid desaturase.

In some embodiments of the methods, the recombinant acyl-lipid desaturase is acyl-lipid desaturase delta-9 (EC: 1.14.19.1), the engineered microorganism produces oleic acid, and the production and secretion into the culture medium of oleic acid is increased in the engineered microorganism relative to production and secretion into the culture medium of oleic acid by an otherwise identical microorganism lacking the recombinant acyl-lipid desaturase delta-9 (EC:1.14.19.1).

In some embodiments of the methods, the engineered microorganism further comprises a recombinant acyl-lipid desaturase delta-12 (EC:1.14.19.6), the engineered microorganism produces linoleic acid, and the production and secretion into the culture medium of linoleic acid is increased in the engineered microorganism relative to production and secretion into the culture medium of linoleic acid by an otherwise identical microorganism lacking at least one of the recombinant acyl-lipid desaturase delta-9 (EC:1.14.19.1) and the recombinant acyl-lipid desaturase delta-12 (EC:1.14.19.6).

In some embodiments of the methods, the engineered microorganism further comprises a recombinant acyl-lipid desaturase delta-15 (EC:1.14.19.-), the engineered microorganism produces α-linolenic acid, and the production and secretion into the culture medium of α-linolenic acid is increased in the engineered microorganism relative to production and secretion into the culture medium of α-linolenic acid by an otherwise identical microorganism lacking at least one of the recombinant acyl-lipid desaturase delta-9 (EC: 1.14.19.1), the recombinant acyl-lipid desaturase delta-12 (EC:1.14.19.6), and the recombinant acyl-lipid desaturase delta-15 (EC:1.14.19.-).

In some embodiments of the methods, the microorganism is a bacterium. In some embodiments the bacterium is a cyanobacterium. In some embodiments the bacterium is *Escherichia coli*.

Also provided herein are engineered microorganisms. In some embodiments, the engineered microorganisms comprise at least one recombinant nucleic acid encoding an acyl-lipid desaturase specific for a substrate comprising at least 18 carbon atoms. In some embodiments, the engineered microorganism further comprises a recombinant nucleic acid encoding a thioesterase (EC:3.1.2.14). In some embodiments, the at least one acyl-lipid desaturase specific for a substrate comprising at least 18 carbon atoms is selected from acyl-lipid desaturase delta-9 (EC:1.14.19.1), acyl-lipid desaturase delta-12 (EC:1.14.19.6), and acyl-lipid desaturase delta-15 (EC:1.14.19.-).

In some embodiments of the engineered microorganisms, the acyl-lipid desaturase specific for a substrate comprising at least 18 carbon atoms is acyl-lipid desaturase delta-9 (EC: 1.14.19.1). In some embodiments, the engineered microorganism further comprises a recombinant nucleic acid encoding acyl-lipid desaturase delta-12 (EC:1.14.19.6). In some embodiments, the engineered microorganism further comprises a recombinant nucleic acid encoding acyl-lipid desaturase delta-15 (EC:1.14.19.-).

In some embodiments of the engineered microorganisms, the engineered microorganism further comprises one or more recombinant nucleic acid that together encode subunits accB, accC, accD, and accA of the acetyl-CoA carboxylase enzyme (EC:6.4.1.2).

In some embodiments of the engineered microorganisms, the engineered microorganism further comprises at least one genetic modification that reduces or eliminates production of at least one protein selected from phosphoenolpyruvate carboxylase (EC 4.1.1.31), NAD+-dependent D-lactate dehydrogenase (EC 1.1.1.28), 2-isopropylmalate synthase (EC 2.3.3.13), citrate (Si)-synthase (EC 2.3.3.1), acetyl-CoA C-acetyltransferase (EC 2.3.1.9), phosphate acetyltransferase (EC 2.3.1.8), and acetate kinase (EC 2.7.2.1).

In some embodiments of the engineered microorganisms, the engineered microorganism further comprises at least one genetic modification that reduces or eliminates production of acyl-ACP synthetase (EC:6.2.1.20) in the engineered microorganism. In some embodiments, the recombinant nucleic acid encoding a thioesterase (EC:3.1.2.14) encodes a recombinant thioesterase (EC:3.1.2.14) localized to the cytosol of the engineered microorganism In some embodiments of the engineered microorganism, the at least one recombinant acyl-lipid desaturase specific for a substrate comprising at least 18 carbon atoms is selected from acyl-lipid desaturase delta-9 (EC:1.14.19.1), acyl-lipid desaturase delta-12 (EC:1.14.19.6), and acyl-lipid desaturase delta-15 (EC:1.14.19.-). In some embodiments, the recombinant acyl-lipid desaturase specific for a substrate comprising at least 18 carbon atoms is acyl-lipid desaturase delta-9 (EC: 1.14.19.1). In some embodiments, the engineered microorganism further comprises a recombinant nucleic acid encoding acyl-lipid desaturase delta-12 (EC:1.14.19.6). In some embodiments, the engineered microorganism further comprises a recombinant nucleic acid encoding acyl-lipid desaturase delta-15 (EC:1.14.19.-).

In some embodiments of the engineered microorganisms, the engineered microorganism further comprises at least one genetic modification that increases, decreases, or eliminates production of at least one component of at least one polar cell layer of the engineered microorganism.

In some embodiments of the engineered microorganisms, the microorganism is a bacterium. In some embodiments, the bacterium is a cyanobacterium. In some embodiments, the bacterium is *Escherichia coli*.

Also provided are unsaturated free fatty acids comprising at least 18 carbon atoms, produced by the methods described herein. In some embodiments, the unsaturated free fatty acid comprising at least 18 carbon atoms is selected from oleic acid, linoleic acid and α-linolenic acid.

Also provided are methods of making a mixture of at least two free fatty acids. In some embodiments, the method comprises culturing at least one engineered microorganism comprising at least one recombinant nucleic acid encoding an acyl-lipid desaturase specific for a substrate comprising at least 18 carbon atoms under appropriate conditions to produce the at least two free fatty acids, isolating the at least two free fatty acids from the cultured at least one engineered microorganism, and formulating the mixture of at least two free fatty acids. In some embodiments, the mixture has a composition similar to that of a seed oil. In some embodiments, at least two engineered microorganisms are cultured separately, at least one free fatty acid is isolated from each culture, and the formulating comprises mixing the at least one free fatty acid isolated from each of the at least two cultures. In some embodiments, the seed oil is selected from coconut oil, cottonseed oil, flaxseed oil, grapeseed oil, corn (maize) oil, palm oil, palm olein, palm kernel oil, peanut oil, rapeseed oil, sesame seed oil, soybean oil and sunflower seed oil. In some embodiments, the engineered microorganism further comprises a recombinant nucleic acid encoding a thioesterase (EC:3.1.2.14). In some embodiments, the at least one acyl-lipid desaturase specific for a substrate comprising at least 18 carbon atoms is selected from acyl-lipid desaturase delta-9 (EC:1.14.19.1), acyl-lipid desaturase delta-12 (EC: 1.14.19.6), and acyl-lipid desaturase delta-15 (EC:1.14.19.-).

Also provided are mixtures of at least two free fatty acids produced by the methods disclosed herein.

DETAILED DESCRIPTION

Figure 1:
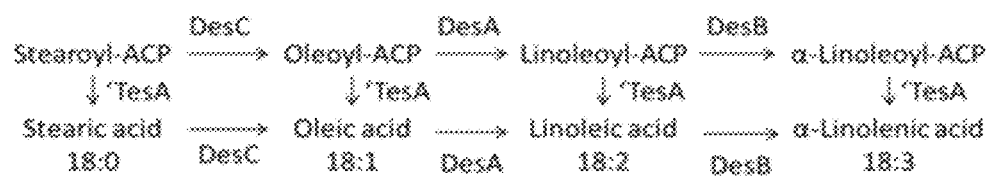
FIG. 1 shows pathways for synthesis of the C18 free fatty acids stearic acid, oleic acid, linoleic acid, and alpha-linolenic acid by microorganisms disclosed herein.

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all Genbank records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3d ed., Cold Spring Harbor Laboratory Press, Cold Spring Harbor, N.Y. (2001); Ausubel et al., Current Protocols in Molecular Biology, Greene Publishing Associates (1992, and Supplements to 2002); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999). Many molecular biology and genetic techniques applicable to cyanobacteria are described in Heidorn et al., "Synthetic Biology in Cyanobacteria: Engineering and Analyzing Novel Functions," Methods in Enzymology, Vol. 497, Ch. 24 (2011), which is hereby incorporated herein by reference.

The term "comprising" as used herein is synonymous with "including" or "containing", and is inclusive or open-ended and does not exclude additional, unrecited members, elements or method steps.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

A "synthetic" RNA, DNA or a mixed polymer is one created outside of a cell, for example one synthesized chemically.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" biomolecule (e.g., a fatty acid) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules can be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, for example, if it is synthesized from an mRNA synthesized from a recombinant gene present in the cell.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

The term "deletion" as used herein refers to the removal of one or more nucleotides from a nucleic acid molecule or one or more amino acids from a protein, the regions on either side being joined together.

The term "knock-out" as used herein refers to gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a nonsense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

Promoters useful for expressing the recombinant genes described herein include both constitutive and inducible/repressible promoters. Examples of inducible/repressible promoters include nickel-inducible promoters (e.g., PnrsA, PnrsB; see, e.g., Lopez-Mauy et al., Cell (2002) v.43:247-256) and urea repressible promoters such as PnirA (described in, e.g., Qi et al., Applied and Environmental Microbiology (2005) v.71: 5678-5684). In other embodiments, a PaphII and/or a lacIq-Ptrc promoter can used to control expression. Where multiple recombinant genes are expressed in an engineered microorganism of the invention, the different genes can be controlled by different promoters or by identical promoters in separate operons, or the expression of two or more genes may be controlled by a single promoter as part of an operon.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as 125I, 32P, 35S, and 3H, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. Fusions that include the entirety of the proteins of the present invention have particular utility. The heterologous polypeptide included within the fusion protein of the present invention is at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. In some embodiments, a mutein has at least 90% overall sequence homology to the wild-type protein. In other embodiments, a mutein exhibits at least 95% sequence identity, or 98%, or 99%, or 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, or at least about 20 residues, or at least about 24 residues, or at least about 28 residues, or more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

A. Unsaturated Free Fatty Acids

Oleic acid, linoleic acid, and alpha-linoleic acid are unsaturated free fatty acids (FFAs) comprising 18 carbon atoms. Oleic acid has a single double bond at the alpha-9 position. Linoleic acid has two double bonds, at the alpha-9 and alpha-12 positions. Finally, alpha-linolenic acid has three double bonds, at the alpha-9, alpha-12, and alpha-15 positions.

These FFAs are synthesized from stearic acid by acyl-lipid desaturases and thioesterase. The synthesis pathways are shown in FIG. 1. The thioesterase enzyme (encoded by the *E. coli* TesA gene, for example) converts palmitoyl-ACP, stearoyl-ACP, oleoyl-ACP, and linoleoyl-ACP and alpha-linolenoyl-ACP into palmitate(16:0), stearate(18:0), oleate (18:1), linoleate(18:2) and alpha-linolenate(18:3). As shown in FIG. 1, acyl-lipid desaturase delta-9 (EC:1.14.19.1) (encoded by desC, for example) converts stearoyl-ACP to oleoyl-ACP and also converts stearate to oleate; acyl-lipid desaturase delta-12 (EC:1.14.19.6) (encoded by desA, for example) converts oleoyl-ACP to linoleoyl-ACP and also converts oleate to linoleate; and acyl-lipid desaturase delta-15 (EC:1.14.19.-) converts linoleoyl-ACP to alpha-linoleoyl-ACP and also converts linoleate to alpha-linolenate. As shown in FIG. 1, these enzymes provide multiple different pathways for the synthesis of oleic acid, linoleic acid, and alpha-linoleic acid from stearoyl-ACP.

B. Unsaturated Free Fatty Acid Synthetic Proteins and Nucleic Acids.

Several exemplary genes and proteins involved in the synthesis of free fatty acids are provided herein.

Acyl-lipid desaturase enzymes introduce a double bond into the carbon backbone of a fatty acid molecule. In some embodiments the acyl-lipid desaturase is an acyl-lipid desaturase delta-9 (EC:1.14.19.1). In some embodiments the acyl-lipid desaturase is an acyl-lipid desaturase delta-9 protein listed in Table 1. In some embodiments the acyl-lipid desaturase is a modified derivative or mutein of an acyl-lipid desaturase delta-9 protein listed in Table 1. In some embodiments the acyl-lipid desaturase delta-9 protein is encoded by a gene listed in Table 1. In some embodiments the acyl-lipid desaturase delta-9 protein is encoded by a degenerate variant of a gene listed in Table 1. In some embodiments the acyl-lipid desaturase delta-9 protein is encoded by a gene that encodes a modified derivative or mutein of an acyl-lipid desaturase delta-9 protein listed in Table 1. In some embodiments the acyl-lipid desaturase delta-9 protein is encoded by a gene that has substantial homology to a gene listed in Table 1. An exemplary full length codon optimized nucleic acid sequence for a gene encoding an acyl-lipid desaturase delta-9 is presented as SEQ ID NO: 3.

TABLE 1

Exemplary Δ9 Genes and Proteins

| Source | Genbank Gene Accession Number | Genbank Protein Accession Number |
|---|---|---|
| Anabaena sp. PCC 7120 | NC_003272 | NP_489031 |
| Anabaena sp. PCC 7120 | NC_003272 | NP_485639 |
| Anabaena variabilis ATCC 29413 | NC_007413 | YP_322790 |
| Anabaena variabilis ATCC 29413 | NC_007413 | YP_324706 |
| Crocosphaera watsonii WH 8501 | NZ_AADV02000119 | ZP_00518170 |
| Gloeobacter violaceus strain PCC 7421 | NC_005125 | NP_925812 |
| Gloeobacter violaceus strain PCC 7421 | NC_005125 | NP_924181 |
| Gloeobacter violaceus strain PCC 7421 | NC_005125 | NP_924892 |
| Gloeobacter violaceus strain PCC 7421 | NC_005125 | NP_924893 |
| Gloeobacter violaceus strain PCC 7421 | NC_005125 | NP_924884 |
| Gloeobacter violaceus strain PCC 7421 | NC_005125 | NP_924886 |
| Nostoc punctiforme ATCC 29133(PCC 73102) | NZ_AAAY02000002 | ZP_00345918 |
| Nostoc punctiforme ATCC 29133(PCC 73102) | NZ_AAAY02000046 | ZP_00108582 |
| Prochlorococcus marinus str. NATL1A | NC_008819 | YP_001015962 |
| Prochlorococcus marinus strain NATL2A | NC_007335 | YP_292464 |
| Prochlorococcus marinus MIT 9211 | NZ_AALP01000001 | ZP_01006363 |
| Prochlorococcus marinus str. MIT 9301 | NC_009091 | YP_001092086 |
| Prochlorococcus marinus str. MIT 9303 | NC_008820 | YP_001018890 |
| Prochlorococcus marinus str. MIT 9303 | NC_008820 | YP_001018888 |
| Prochlorococcus marinus str. MIT 9312 | NC_007577 | YP_398261 |
| Prochlorococcus marinus str. MIT 9313 | NC_005071 | NP_895996 |
| Prochlorococcus marinus str. MIT 9313 | NC_005071 | NP_895998 |
| Prochlorococcus marinus str. AS9601 | NC_008816 | YP_001010271 |
| Prochlorococcus marinus str. MIT 9515 | NC_008817 | YP_001012176 |
| Prochlorococcus marinus subsp. marinus str. CCMP1375 (SS120) | NC_005042 | NP_876224 |
| Prochlorococcus marinus subsp. marinus str. CCMP1986 (MED4) | NC_005072 | NP_893789 |
| Synechococcus elongates strain PCC 7942 | NC_007604 | YP_401578 |
| Synechococcus elongates strain PCC 6301 | NC_006576 | YP_172259 |
| Synechococcus sp. BL107 | NZ_AATZ01000002 | ZP_01469203 |
| Synechococcus sp. BL107 | NZ_AATZ01000002 | ZP_01469204 |
| Synechococcus sp. CC9311 | NC_008319 | YP_731981 |
| Synechococcus sp. CC9311 | NC_008319 | YP_731979 |
| Synechococcus sp. CC9605 | NC_007516 | YP_382824 |
| Synechococcus sp. CC9902 | NC_007513 | YP_378192 |
| Synechococcus sp. CC9902 | NC_007513 | YP_378193 |
| Synechococcus sp. JA-2-3Ba(2-13) | NC_007776 | YP_477105 |

TABLE 1-continued

Exemplary Δ9 Genes and Proteins

| Source | Genbank Gene Accession Number | Genbank Protein Accession Number |
|---|---|---|
| Synechococcus sp. JA-3-3Ab | NC_007775 | YP_475739 |
| Synechococcus sp. RCC307 | NC_009482 | YP_001228651 |
| Synechococcus sp. RCC307 | NC_009482 | YP_001228649 |
| Synechococcus sp. RS9916 | NZ_AAUA01000001 | ZP_01471384 |
| Synechococcus sp. RS9916 | NZ_AAUA01000001 | ZP_01471382 |
| Synechococcus sp. RS9917 | NZ_AANP01000001 | ZP_01079314 |
| Synechococcus sp. RS9917 | NZ_AANP01000001 | ZP_01079312 |
| Synechococcus sp. WH 5701 | NZ_AANO01000004 | ZP_01084898 |
| Synechococcus sp. WH 5701 | NZ_AANO01000004 | ZP_01084896 |
| Synechococcus sp. WH 7803 | NC_009481 | YP_001226140 |
| Synechococcus sp. WH 7803 | NC_009481 | YP_001226138 |
| Synechococcus sp. WH 7805 | NZ_AAOK01000005 | ZP_01125021 |
| Synechococcus sp. WH 7805 | NZ_AAOK01000005 | ZP_01125023 |
| Synechococcus sp. WH 8102 | NC_005070 | NP_898466 |
| Synechocystis sp. PCC 6803 | NC_000911 | NP_442430 |
| Thermosynechococcus elongatus strain BP-1 | NC_004113 | NP_682509 |
| Thermosynechococcus elongatus strain BP-1 | NC_004113 | NP_683170 |
| Thermosynechococcus elongatus strain BP-1 | NC_004113 | NP_682443 |
| Trichodesmium erythraeum IMS101 | NC_008312 | YP_721205 |
| Lyngbya sp. PCC 8106 | NZ_AAVU01000086 | ZP_01624678 |
| Nodularia spumigena CCY9414 | NZ_AAVW01000082 | ZP_01631817 |
| Nodularia spumigena CCY9414 | NZ_AAVW01000142 | ZP_01632615 |
| Cyanothece sp. CCY0110 | NZ_AAXW01000001 | ZP_01726409 |
| Cyanothece sp. CCY0110 | NZ_AAXW01000014 | ZP_01729213 |

In some embodiments the acyl-lipid desaturase is an acyl-lipid desaturase delta-12 (EC:1.14.19.6). In some embodiments the acyl-lipid desaturase is an acyl-lipid desaturase delta-12 protein listed in Table 2. In some embodiments the acyl-lipid desaturase is a modified derivative or mutein of an acyl-lipid desaturase delta-12 protein listed in Table 2. In some embodiments the acyl-lipid desaturase delta-12 protein is encoded by a gene listed in Table 2. In some embodiments the acyl-lipid desaturase delta-12 protein is encoded by a degenerate variant of a gene listed in Table 2. In some embodiments the acyl-lipid desaturase delta-12 protein is encoded by a gene that encodes a modified derivative or mutein of an acyl-lipid desaturase delta-12 protein listed in Table 2. In some embodiments the acyl-lipid desaturase delta-12 protein is encoded by a gene that has substantial homology to a gene listed in Table 2. An exemplary full length codon optimized nucleic acid sequence for a gene encoding an acyl-lipid desaturase delta-12 is presented as SEQ ID NO: 1.

TABLE 2

Exemplary Δ12 Genes and Proteins

| Source | Genbank Gene Accession Number | Genbank Protein Accession Number |
|---|---|---|
| Anabaena sp. PCC 7120 | NC_003272 | NP_485638 |
| Anabaena variabilis ATCC 29413 | NC_007413 | YP_324705 |
| Crocosphaera watsonii WH 8501 | NZ_AADV02000040 | ZP_00516843 |
| Crocosphaera watsonii WH 8501 | NZ_AADV02000003 | ZP_00515010 |
| Gloeobacter violaceus strain PCC 7421 | NC_005125 | NP_925569 |

TABLE 2-continued

Exemplary Δ12 Genes and Proteins

| Source | Genbank Gene Accession Number | Genbank Protein Accession Number |
|---|---|---|
| Gloeobacter violaceus strain PCC 7421 | NC_005125 | NP_926681 |
| Nostoc punctiforme ATCC 29133 (PCC 73102) | NZ_AAAY02000046 | ZP_00108583 |
| Prochlorococcus marinus str. NATL1A | NC_008819 | YP_001014905 |
| Prochlorococcus marinus strain NATL2A | NC_007335 | YP_291588 |
| Prochlorococcus marinus MIT 9211 | NZ_AALP01000001 | ZP_01005647 |
| Prochlorococcus marinus MIT 9211 | NZ_AALP01000001 | ZP_01005648 |
| Prochlorococcus marinus str. MIT 9301 | NC_009091 | YP_001091800 |
| Prochlorococcus marinus str. MIT 9301 | NC_009091 | YP_001091796 |
| Prochlorococcus marinus str. MIT 9303 | NC_008820 | YP_001017424 |
| Prochlorococcus marinus str. MIT 9303 | NC_008820 | YP_001018108 |
| Prochlorococcus marinus str. MIT 9312 | NC_007577 | YP_397972 |
| Prochlorococcus marinus str. MIT 9312 | NC_007577 | YP_397969 |
| Prochlorococcus marinus str. MIT 9313 | NC_005071 | NP_894082 |
| Prochlorococcus marinus str. MIT 9313 | NC_005071 | NP_894629 |
| Prochlorococcus marinus str. AS9601 | NC_008816 | YP_001009982 |
| Prochlorococcus marinus str. AS9601 | NC_008816 | YP_001009977 |
| Prochlorococcus marinus str. MIT 9515 | NC_008817 | YP_001011874 |
| Prochlorococcus marinus str. MIT 9515 | NC_008817 | YP_001011866 |
| Prochlorococcus marinus subsp. marinus str. CCMP1375 (SS120) | NC_005042 | NP_875600 |
| Prochlorococcus marinus subsp. marinus str. CCMP1375 (SS120) | NC_005042 | NP_875606 |
| Prochlorococcus marinus subsp. marinus str. CCMP1986 (MED4) | NC_005072 | NP_893499 |
| Prochlorococcus marinus subsp. marinus str. CCMP1986 (MED4) | NC_005072 | NP_893495 |
| Synechococcus sp. BL107 | NZ_AATZ01000002 | ZP_01468963 |
| Synechococcus sp. CC9311 | NC_008319 | YP_729627 |
| Synechococcus sp. CC9605 | NC_007516 | YP_382268 |
| Synechococcus sp. CC9902 | NC_007513 | YP_376159 |
| Synechococcus sp. RCC307 | NC_009482 | YP_001228013 |
| Synechococcus sp. RS9917 | NZ_AANP01000005 | ZP_01080849 |
| Synechococcus sp. WH 5701 | NZ_AANO01000002 | ZP_01083974 |
| Synechococcus sp. WH 5701 | NZ_AANO01000079 | ZP_01086617 |
| Synechococcus sp. WH 7803 | NC_009481 | YP_001224312 |
| Synechococcus sp. WH 7805 | NZ_AAOK01000004 | ZP_01124768 |
| Synechococcus sp. WH 7805 | NZ_AAOK01000004 | ZP_01124517 |
| Synechococcus sp. WH 8102 | NC_005070 | NP_896789 |
| Synechococcus sp. WH 8102 | NC_005070 | NP_897787 |
| Synechocystis sp. PCC 6803 | NC_000911 | NP_441489 |
| Trichodesmium erythraeum IMS101 | NC_008312 | YP_720110 |
| Lyngbya sp. PCC 8106 | NZ_AAVU01000015 | ZP_01621185 |
| Nodularia spumigena CCY9414 | NZ_AAVW01000142 | ZP_01632616 |
| Cyanothece sp. CCY0110 | NZ_AAXW01000104 | ZP_01732458 |

In some embodiments the acyl-lipid desaturase is an acyl-lipid desaturase delta-15 (EC:1.14.19.-). In some embodiments the acyl-lipid desaturase is an acyl-lipid desaturase delta-15 protein listed in Table 3. In some embodiments the acyl-lipid desaturase is a modified derivative or mutein of an acyl-lipid desaturase delta-15 protein listed in Table 3. In some embodiments the acyl-lipid desaturase delta-15 protein is encoded by a gene listed in Table 3. In some embodiments the acyl-lipid desaturase delta-15 protein is encoded by a degenerate variant of a gene listed in Table 3. In some embodiments the acyl-lipid desaturase delta-15 protein is encoded by a gene that encodes a modified derivative or mutein of an acyl-lipid desaturase delta-15 protein listed in Table 3. In some embodiments the acyl-lipid desaturase delta-15 protein is encoded by a gene that has substantial homology to a gene listed in Table 3. An exemplary full length codon optimized nucleic acid sequence for a gene encoding an acyl-lipid desaturase delta-is presented as SEQ ID NO: 2.

TABLE 3

Exemplary Δ15 Genes and Proteins

| Source | Genbank Gene Accession Number | Genbank Protein Accession Number |
|---|---|---|
| Anabaena sp. PCC 7120 | NC_003272 | NP_485637 |
| Anabaena variabilis ATCC 29413 | NC_007413 | YP_324704 |
| Crocosphaera watsonii WH 8501 | NZ_AADV02000017 | ZP_00516181 |
| Nostoc punctiforme ATCC 29133(PCC 73102) | NZ_AAAY02000046 | ZP_00108584 |
| Synechococcus sp. WH 7803 | NC_009481 | YP_001225348 |
| Synechocystis sp. PCC 6803 | NC_000911 | NP_441622 |
| Trichodesmium erythraeum IMS101 | NC_008312 | YP_723951 |
| Lyngbya sp. PCC 8106 | NZ_AAVU01000077 | ZP_01624560 |
| Nodularia spumigena CCY9414 | NZ_AAVW01000142 | ZP_01632617 |
| Cyanothece sp. CCY0110 | NZ_AAXW01000009 | ZP_01728541 |

Additional information regarding the acyl-lipid desaturase genes and proteins listed in Tables 1-3 is provided by Chi et al., Comparative and Functional Genomics, 2008:284508, Epub 2008 Dec. 2, which is incorporated herein by reference.

Thioesterases hydrolyze fatty acid esters to yield free fatty acids. In some embodiments the thioesterase (EC:3.1.2.14) is a thioesterase protein listed in Table 4. In some embodiments the thioesterase is a modified derivative or mutein of a thioesterase protein listed in Table 4. In some embodiments the thioesterase protein is encoded by a gene listed in Table 4. In some embodiments the thioesterase protein is encoded by a degenerate variant of a gene listed in Table 4. In some embodiments the thioesterase protein is encoded by a gene that encodes a modified derivative or mutein of a thioesterase protein listed in Table 4. In some embodiments the thioesterase protein is encoded by a gene that has substantial homology to a gene listed in Table 4.

TABLE 4

Exemplary Thioesterase Genes and Proteins

| Source | Genbank Gene Accession Number | Genbank Protein Accession Number |
|---|---|---|
| Arabidopsis thaliana | NM_113415 | NP_189147 |
| Brassica juncea | AJ278479 | CAC14164 |
| E. Coli | L06182 | AAA24664 |

In some embodiments the nucleic acids described above in this Section B are isolated. In some embodiments the nucleic acids are provided in a vector. In some embodiments the nucleic acids are operatively linked to an expression control sequence.

Also provided are vectors, including expression vectors, which comprise at least one of the above nucleic acid molecules, as described further herein. In a first embodiment, the vectors comprise at least one of the isolated nucleic acid molecules described above. In an alternative embodiment, the vectors comprise the above-described nucleic acid molecules operably linked to one or more expression control sequence. The vectors can thus be used to express at least one protein involved in fatty acid biosynthesis, such as a protein selected from an acyl-lipid desaturase (such as an acyl-lipid desaturase selected from acyl-lipid desaturase delta-9 (EC:1.14.19.1), acyl-lipid desaturase delta-12 (EC:1.14.19.6), and acyl-lipid desaturase delta-15 (EC:1.14.19.-); and a thioesterase (EC: 3.1.2.14).

Suitable vectors for expression of nucleic acids in microorganisms are well known to those of skill in the art. Suitable vectors for use in cyanobacteria are described, for example, in Heidorn et al., "Synthetic Biology in Cyanobacteria: Engineering and Analyzing Novel Functions," Methods in Enzymology, Vol. 497, Ch. 24 (2011). Exemplary replicative vectors that can be used for engineering the cyanobacteria disclosed herein include pPMQAK1, pSL1211, pFC1, pSB2A, pSCR119/202, pSUN119/202, pRL2697, pRL25C, pRL1050, pSG111M, and pPBH201. Vectors suitable for other organisms (e.g., *E. coli*) are known in the art.

Other vectors such as pJB161 which are capable of receiving nucleic acid sequences disclosed herein may also be used. Vectors such as pJB161 comprise sequences which are homologous with sequences present in plasmids endogenous to certain photosynthetic microorganisms (e.g., plasmids pAQ1, pAQ3, and pAQ4 of certain *Synechococcus* species). Examples of such vectors and how to use them is known in the art and provided, for example, in Xu et al., "Expression of Genes in Cyanobacteria: Adaptation of Endogenous Plasmids as Platforms for High-Level Gene Expression in *Synechococcus* sp. PCC 7002," Chapter 21 in Robert Carpentier (ed.), "Photosynthesis Research Protocols," Methods in Molecular Biology, Vol. 684, 2011, which is hereby incorporated herein. Recombination between pJB161 and the endogenous plasmids in vivo yield engineered microbes expressing the genes of interest from their endogenous plasmids. Alternatively, vectors can be engineered to recombine with the host cell chromosome, or the vector can be engineered to replicate and express genes of interest independent of the host cell chromosome or any of the host cell's endogenous plasmids.

C. Microorganisms

At least one of the nucleic acids described in Section B above is introduced into host microorganisms to make engineered microorganisms.

1. Types of Host Microorganisms

"Microorganisms" includes prokaryotic and eukaryotic microbial species from the Domains *Archaea, Bacteria* and *Eucarya*, the latter including yeast and filamentous fungi, protozoa, algae, or higher Protista. The terms "microbial cells" and "microbes" are used interchangeably with the term microorganism.

A variety of host microorganisms can be transformed to produce an unsaturated free fatty acid comprising at least 18 carbon atoms. Suitable host microorganisms include both autotrophic and heterotrophic microbes. In some applications, an autotrophic microorganism allows for a reduction in the fossil fuel and/or electricity inputs required to make a given quantity of free fatty acid. This, in turn, may reduce the cost and/or the environmental impact of producing free fatty acids.

Photoautotrophic microrganisms include eukaryotic algae, as well as prokaryotic cyanobacteria, green-sulfur bacteria, green non-sulfur bacteria, purple sulfur bacteria, and purple non-sulfur bacteria.

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C.; and psychrophiles, which grow at or below 15° C. such as *Psychrobacter* and some insects. Radiation tolerant organisms include *Deinococcus radiodurans*. Pressure-tolerant organisms include piezophiles, which tolerate pressure of 130 MPa. Weight-tolerant organisms include barophiles. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt-tolerant organisms include halophiles (e.g., 2-5 M NaCl) *Halobacteriacea* and *Dunaliella salina*. pH-tolerant organisms include alkaliphiles such as *Natronobacterium, Bacillus firmus* OF4, *Spirulina* spp. (e.g., pH >9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas-tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). See, e.g., Gross, Michael. *Life on the Edge: Amazing Creatures Thriving in Extreme Environments*. New York: Plenum (1998); and Seckbach, J. "Search for Life in the Universe with Terrestrial Microbes Which Thrive Under Extreme Conditions" in Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococ-* cum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spennatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepohlia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis, and Zygonium.

Additional cyanobacteria include members of the genus Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Synechocystis, Cyanocystis, Dermocarpella, Stanieria, Xenococcus, Chroococcidiopsis, Myxosarcina,

*Arthrospira, Borzia, Crinalium, Geitlerinemia, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Cyanospira, Cylindrospermopsis, Cylindrospermum, Nodularia, Nostoc, Scylonema, Calothrix, Rivularia, Tolypothrix, Chlorogloeopsis, Fischerella, Geitieria, Iyengariella, Nostochopsis, Stigonema* and *Thermosynechococcus.*

Green non-sulfur bacteria include but are not limited to the following genera: *Chloroflexus, Chloronema, Oscillochloris, Heliothrix, Herpetosiphon, Roseiflexus*, and *Thermomicrobium.*

Green sulfur bacteria include but are not limited to the following genera: *Chlorobium, Clathrochloris*, and *Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic S-Metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

Yet other suitable organisms include synthetic cells or cells produced by synthetic genomes as described in Venter et al. U.S. Pat. Pub. No. 2007/0264688, and cell-like systems or synthetic cells as described in Glass et al. U.S. Pat. Pub. No. 2007/0269862.

Still other suitable organisms include *Escherichia coli, Acetobacter aceti, Bacillus subtilis,* yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis.* In some embodiments those organisms are engineered to fix carbon dioxide while in other embodiments they are not.

2. Engineered Microorganisms

In another aspect of the disclosure, host cells transformed with the nucleic acid molecules and/or vectors described in Section B above, and descendants thereof, are provided. Generally speaking, methods of making an engineered microorganism as disclosed herein are known in the art. A microorganism, such as a cyanobacterium or *E. coli*, is transformed with a nucleic acid construct, such as a vector described herein. Methods of transformation are well known in the art, and may include electroporation, natural transformation, and calcium choloride mediated transformation. Methods of screening for and verifying chromosomal integration are also known in the art.

In some embodiments, a method of making a microorganism disclosed herein comprises first transforming the microorganism with a vector comprising, in part, an antibiotic-resistance marker and a negative selection marker. Chromosomal integration may be selected for by selecting for antibiotic resistance. Next, the antibiotic-resistant strain is transformed with a similar vector comprising the target genes of interest. Chromosomal integration of the target genes may be selected for by selecting for the absence of the negative marker. For instance, if the negative marker is sacB, then one would select for sucrose resistance.

In some embodiments, the engineered microorganisms carry the introduced nucleic acid sequences on vectors, which may but need not be freely replicating vectors. In other embodiments, the nucleic acids are integrated into the genome of the host cells and/or into an endogenous plasmid of the host cells. In some embodiments, at least two nucleic acids described herein (e.g., nucleic acids coding for acyl-lipid desaturase delta-9 (EC:1.14.19.1) and acyl-lipid desaturase delta-12 (EC:1.14.19.6)) are introduced into the engineered host cell. In such embodiments, the at least two nucleic acids can be present on a single DNA molecule, such as a single vector, or may be present in more than one DNA molecule. In some embodiments, n different nucleic acid sequences are introduced, encoding n different proteins, and the n nucleic acid sequences are present on n different nucleic acid molecules in the resulting engineered microorganism. In some embodiments, n is at least 2 and the n nucleic acid sequences are present on fewer than n different nucleic acid molecules in the resulting engineered microorganism. In some embodiments, the introduced nucleic acid sequences are present on 1, 2, 3, 4, 5, 6, 7, 8, 9, 10, or greater different nucleic acid molecules. In some embodiments, the engineered microorganism comprises a nucleic acid molecule comprising heterologous nucleic acid sequences encoding at least 1, 2, 3, 4, 5, 6, 7, 8, 9, 10, or more heterologous proteins. In some embodiments, the engineered microorganism comprises at least 1, 2, 3, 4, 5, 6, 7, 8, 9, 10, or more nucleic acid molecules that together comprise heterologous nucleic acid sequences encoding at least 1, 2, 3, 4, 5, 6, 7, 8, 9, 10, or more heterologous proteins.

In some embodiments, the host cells of the disclosure are mutated by recombination with a disruption, deletion or mutation of the isolated nucleic acid, so that the activity of a native protein involved in fatty acid biosynthesis in the engineered cell is reduced or eliminated compared to a host cell lacking the mutation. In some embodiments, the native protein is selected from an acyl-lipid desaturase (such as an acyl-lipid desaturase selected from acyl-lipid desaturase delta-9 (EC:1.14.19.1), acyl-lipid desaturase delta-12 (EC:1.14.19.6), and acyl-lipid desaturase delta-15 (EC:1.14.19.-)), and a thioesterase (EC:3.1.2.14).

In some embodiments, the introduced nucleic acid sequence encodes a protein that is not naturally present in the host microorganism. In some embodiments, the introduced nucleic acid sequence encodes a protein that differs by least one amino acid from every protein naturally present in the host microorganism. In some embodiments, the introduced nucleic acid sequence encodes a protein that is less than 99%, 98%, 97%, 96%, or 95% identical to every protein naturally present in the host microorganism. In some embodiments, the introduced nucleic acid sequence encodes a protein that is less than 90%, 85%, 80%, 75%, or 70% identical to every protein naturally present in the host microorganism. In some embodiments, the introduced nucleic acid sequence encodes a protein that is naturally present in the host microorganism.

3. Promoters

Promoters useful for expressing the recombinant genes described herein include both constitutive and inducible/repressible promoters. Examples of inducible/repressible promoters include nickel-inducible promoters (e.g., PnrsA, PnrsB; see, e.g., Lopez-Mauy et al., Cell (2002) v.43: 247-256) and urea repressible promoters such as PnirA (described in, e.g., Qi et al., Applied and Environmental Microbiology (2005) v.71: 5678-5684). Additional examples of inducible/repressible promoters include PnirA (promoter that drives expression of the nirA gene, induced by nitrate and repressed by urea) and psuf (promoter that drives expression of the sufA gene, induced by iron stress). Examples of constitutive promoters include pcpc (promoter that drives expression of the cpc operon), prbc (promoter that drives expression of rubisco), ppsbAII (promoter that drives expression of ppsbAII), pero (lambda phage promoter that drives expression of cro). In other embodiments, a PaphII and/or a laclq-Ptrc promoter can used to control expression. Where multiple recombinant genes are expressed in an engineered microorganims of the invention, the different genes can be controlled by different promoters or by identical promoters in separate operons, or the expression of two or more genes may be controlled by a single promoter as part of an operon.

Further non-limiting examples of inducible promoters may include, but are not limited to, those induced by expression of an exogenous protein (e.g., T7 RNA polymerase, SP6 RNA polymerase), by the presence of a small molecule (e.g., IPTG, galactose, tetracycline, steroid hormone, abscisic acid), by absence of small molecules (e.g., $CO_2$, iron, nitrogen), by metals or metal ions (e.g., copper, zinc, cadmium, nickel), and by environmental factors (e.g., heat, cold, stress, light, darkness), and by growth phase. In some embodiments, the inducible promoter is tightly regulated such that in the absence of induction, substantially no transcription is initiated through the promoter. In some embodiments, induction of the promoter does not substantially alter transcription through other promoters. Also, generally speaking, the compound or condition that induces an inducible promoter is not naturally present in the organism or environment where expression is sought.

In some embodiments, the inducible promoter is induced by limitation of $CO_2$ supply to the cyanobacteria culture. By way of non-limiting example, the inducible promoter may be the promoter sequence of Synechocystis PCC 6803 that are up-regulated under the $CO_2$-limitation conditions, such as the crop genes, ntp genes, ndh genes, sbt genes, chp genes, and rbc genes, or a variant or fragment thereof.

In some embodiments, the inducible promoter is induced by iron starvation or by entering the stationary growth phase. In some embodiments, the inducible promoter may be variant sequences of the promoter sequence of cyanobacterial genes that are up-regulated under Fe-starvation conditions such as isiA, or when the culture enters the stationary growth phase, such as isiA, phrA, sigC, sigB, and sigH genes, or a variant or fragment thereof.

In some embodiments, the inducible promoter is induced by a metal or metal ion. By way of non-limiting example, the inducible promoter may be induced by copper, zinc, cadmium, mercury, nickel, gold, silver, cobalt, and bismuth or ions thereof. In some embodiments, the inducible promoter is induced by nickel or a nickel ion. In some embodiments, the inducible promoter is induced by a nickel ion, such as $Ni^{2+}$. In another exemplary embodiment, the inducible promoter is the nickel inducible promoter from Synechocystis PCC 6803. In another embodiment, the inducible promoter may be induced by copper or a copper ion. In yet another embodiment, the inducible promoter may be induced by zinc or a zinc ion. In still another embodiment, the inducible promoter may be induced by cadmium or a cadmium ion. In yet still another embodiment, the inducible promoter may be induced by mercury or a mercury ion. In an alternative embodiment, the inducible promoter may be induced by gold or a gold ion. In another alternative embodiment, the inducible promoter may be induced by silver or a silver ion. In yet another alternative embodiment, the inducible promoter may be induced by cobalt or a cobalt ion. In still another alternative embodiment, the inducible promoter may be induced by bismuth or a bismuth ion.

In some embodiments, the promoter is induced by exposing a cell comprising the inducible promoter to a metal or metal ion. The cell may be exposed to the metal or metal ion by adding the metal to the microbial growth media. In certain embodiments, the metal or metal ion added to the microbial growth media may be efficiently recovered from the media. In other embodiments, the metal or metal ion remaining in the media after recovery does not substantially impede downstream processing of the media or of the bacterial gene products.

Further non-limiting examples of constitutive promoters include constitutive promoters from Gram-negative bacteria or a bacteriophage propogating in a Gram-negative bacterium. For instance, promoters for genes encoding highly expressed Gram-negative gene products may be used, such as the promoter for Lpp, OmpA, rRNA, and ribosomal proteins. Alternatively, regulatable promoters may be used in a strain that lacks the regulatory protein for that promoter. For instance $P_{lac}$, $P_{tac}$, and $P_{tac}$, may be used as constitutive promoters in strains that lack LacI. Similarly, P22 $P_R$ and $P_L$ may be used in strains that lack the lambda C2 repressor protein, and lambda $P_R$ and $P_L$ may be used in strains that lack the lambda C1 repressor protein. In one embodiment, the constitutive promoter is from a bacteriophage. In another embodiment, the constitutive promoter is from a Salmonella bacteriophage. In yet another embodiment, the constitutive promoter is from a cyanophage. In some embodiments, the constitutive promoter is a Synechocystis promoter. For instance, the constitutive promoter may be the PpsbAll promoter or its variant sequences, the Prbc promoter or its variant sequences, the $P_{cpc}$ promoter or its variant sequences, and the PrnpB promoter or its variant sequences.

4. Media and Culture Conditions

One skilled in the art will recognize that a variety of media and culture conditions can be used in conjunction with the methods and engineered microorganisms disclosed herein for the bioproduction of free fatty acids (see, e.g., Rogers and Gallon, Biochemistry of the Algae and Cyanobacteria, Clarendon Press Oxford (1988); Burlwe, Algal Culture: From Laboratory to Pilot Plant, Carnegie Institution of Washington Publication 600 Washington, D.C., (1961); and Round, F. E. The Biology of the Algae. St Martin's Press, New York, 1965; Golden S. S. et al. (1987) Methods Enzymol 153:215-231; Golden and Sherman, J. Bacteriology 158:36 (1984), each of which is incorporated herein by reference). Exemplary culture conditions and media are also described in, e.g., WO/2010/068288, filed May 21, 2009, published Jun. 17, 2010. Typical culture conditions for certain embodiments of the methods of this disclosure include the use of JB 2.1 culture media or A+ media. A recipe for one liter of JB 2.1 appears in Table A, of US 2011/0111470 A1, which table is hereby incorporated herein by reference. In some embodiments at least one additional component is added to the culture medium.

In some embodiments of the methods, the engineered microorganism is cultured for bioproduction of free fatty acids at 15° C. or less. In some embodiments, the engineered microorganism is cultured at from 15° C. to 20° C. In some embodiments, the engineered microorganism is cultured at from 20° C. to 25° C. In some embodiments, the engineered microorganism is cultured at from 25° C. to 30° C. In some embodiments, the engineered microorganism is cultured at from 30° C. to 35° C. In some embodiments, the engineered microorganism is cultured at from 35° C. to 40° C. In some embodiments, the engineered microorganism is cultured at 40° C. or higher. In some embodiments, the engineered microorganism is cultured at 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C., for example.

5. Modifications to Fatty Acid Secretion Pathways

In some embodiments, the engineered microorganims comprises at least one modification to enable and/or increase fatty acid secretion. In some embodiments, a polar cell layer of the microorganism is altered so as to increase fatty acid secretion. By way of example, the peptidoglycan layer, the outer membrane layer, and/or the S layer of the microorganism can be altered to enable increased fatty acid secretion. For instance, the expression of a nucleic acid encoding an S-layer protein, such as sll1951, can be decreased or eliminated. In some embodiments the microorganism comprises the mutation delta-sll1951.

In some embodiments, the polypeptidoglycan layer of the engineered microorganism is weakened to enable increased fatty acid secretion. Methods of weakening the polypeptidoglycan layer are known in the art and include administering an antibiotic, such as ampicillin, to the microorganims. Care should be taken, however, to balance the ability to secrete fatty acids with the potential for cell lysis. Such a balance may be experimentally using methods known in the art.

In some embodiments, the peptidoglycan layer is weakened by down-regulating the transcription efficiency of nucleic acids encoding protein involved in peptidoglycan synthesis, such as those in the mur (e.g., slr0017, slr1423, slr656 and sll2010) and ldh (e.g., slr0528 and slr1656) families to weaken the polypeptidoglycan layer structures. In another embodiment, a nucleic acid encoding a penicillin-binding protein such as ftsI (sll1833), mrcB (slr1710) and ponA (sll0002) is deleted or modified. These proteins are required for the assembly of the peptidoglycan.

In other embodiments, peptidoglycan synthesis is interfered with by substituting a nucleic acid for a central step in an essential pathway with one from another microorganism species, such as using an exogenous asd or alr gene. In other embodiments, the one or more nucleic acid sequence encoding an endolysin from a bacteriophage is introduced. Such a nucleic acid sequence may then be expressed at low levels. Endolysins are peptidoglycan-degrading enzymes that attack the covalent linkages of the peptidoglycans that maintain the integrity of the cell wall. For instance, the endolysin gp19 from *Salmonella* phage P22 is able to degrade *Synechocystis* 6803 polypeptidoglycan layers, and the endolysin R from *E. coli* phage A is able to compromise *Synechocystis* 6803 polypeptidoglycan layers. In some embodiments, these sequences are expressed with different promoters with variant low transcription efficiencies to limit adverse growth effects, for example.

In some embodiments, fatty acid secretion is increased by modifying a genetically engineered strain to express or overexpress a nucleic acid sequence encoding a transporter or porin to make channels for the lipid. Many transport and efflux proteins serve to excrete a large variety of compounds, and these can possibly be modified to be selective for fatty acids. For example, *E. coli* outer membrane protein FadL is a membrane-bound fatty acid transporter, which binds long chain fatty acid with a high affinity. Other suitable transport proteins include efflux proteins and fatty acid transporter proteins (FATP). Suitable non-limiting examples may be found in Table 9 of WO 2011/059745, for example.

6. Modifications to Increase Fatty Acid Release From Cellular Membranes

In some embodiments, the engineered microorganims comprises at least one modification to increase fatty acid release from cellular membranes. In some embodiments, the regulated expression of a nucleic acid encoding a protein capable of hydrolyzing the lipid membranes to free fatty acids in introduced into the engineered microorganims to disrupt the cells and release intracellular fatty acids. Hence, in one embodiment, the enginnered microorganism comprises an inducible promoter operably-linked to a nucleic acid encoding a first protein capable of hydrolyzing the lipid membranes of the microorganims and at least one endolysin protein. In another embodiment, the engineered microorganism comprises a first nucleic acid, wherein the first nucleic acid comprises a first inducible promoter operably-linked to a nucleic acid encoding a first protein capable of hydrolyzing the lipid membranes of the microorganism; and a second nucleic acid, wherein the second nucleic acid comprises a second promoter operably-linked to a nucleic acid encoding at least one endolysin protein.

In some embodiments, the engineered microorganism comprises more than one integrated nucleic acid construct for increasing release of fatty acids from cellular membranes. For instance, in some embodiments the engineered microorganism comprises a first inducible promoter operably-linked to a nucleic acid encoding a first protein capable of hydrolyzing the lipid membranes of the microorganism, a second inducible promoter operably-linked to a different nucleic acid encoding a second protein capable of hydrolyzing the lipid membranes of the microorganism, and at least two endolysin proteins. In a further embodiment, the nucleic acid sequences encoding the endolysin proteins are operably linked to a constitutive promoter.

7. Other Modifications to Increase Fatty Acid Production

Acetyl-CoA carboxylase enzyme (EC:6.4.1.2) is an entry enzyme of the fatty acid biosynthesis and comprised of four subunits encoded by accB, accC, accD, and accA. Accordingly, increasing the expression level of this enzyme can increase fatty acid production in an engineered microorganism. In some embodiments these four genes are overexpressed in an engineered microorganism disclosed herein to increase fatty acid biosynthesis.

Certain intermediates in fatty acid biosynthesis are also involved in other biosynthetic pathways in microorganisms. Reducing or eliminating diversion of at least one of the intermediates to these pathways can increase production of fatty acids by an engineered microorganism disclosed herein. In order to inhibit or reduce the diversion of flux from different intermediates including 3-phosphoglycerate (3-PGA), phosphoenolpyruvate (PEP), pyruvate and acetyl-CoA of the pathway, production of at least one protein selected from phosphoenolpyruvate carboxylase (EC 4.1.1.31), NAD+-dependent D-lactate dehydrogenase (EC 1.1.1.28), 2-isopropylmalate synthase (EC 2.3.3.13), citrate (Si)-synthase (EC 2.3.3.1), acetyl-CoA C-acetyltransferase (EC 2.3.1.9), phosphate acetyltransferase (EC 2.3.1.8), and acetate kinase (EC 2.7.2.1) is reduced or eliminated in the engineered microorganism. In some embodiments, at least one gene selected from ppc, ddh, leu, glt, thl, pta and ack is down-regulated or deleted from the chromosome of respective microorganism.

In some embodiments the engineered microorganism comprises a recombinant thioesterase (EC:3.1.2.14). In some embodiments the recombinant thioesterase (EC:3.1.2.14) is localized to the cytosol. In some embodiments this is accomplished by deleting the leader sequence that triggers the enzyme to be transported to the periplasm. Localization of the enzyme to the cytosol increases secretion of free fatty acids and, in some embodiments, increases the levels and/or ease of isolation free fatty acids produced and/or recovered from a culture of engineered microorganisms.

D. Isolation of Fatty Acids

In some embodiments, the engineered microorganism produces an amount of an unsaturated free fatty acid, such as an unsaturated free fatty acid comprising at least 18 or at least 20 carbon atoms, which is increased relative to the amount of the unsaturated free fatty acid produced by an otherwise identical microorganism. In some embodiments, the otherwise identical microorganism does not produce the at least one unsaturated free fatty acid. In some embodiments, the amount of the at least one unsaturated free fatty acid produced by the otherwise identical microorganism is below the detection limit of the detection technique or assay. In some embodiments, the amount of the at least one unsaturated free fatty acid produced by the engineered microorganism is increased compared to the otherwise identical microorganism by a factor of at least 10%, at least 20%, at least 30%, at least 40%, at least 50%, at least 60%, at least 70%, at least 80%, at least 90%, at least 100%, at least 150%, at least 200%, at least 300%, at least 400%, at least 500%, at least 600%, at least 700%, at least 800%, at least 900%, or at least 1,000% (i.e., 10 fold) or more. In some embodiments, the amount of the at least one unsaturated free fatty acid produced by the engineered microorganism is at least 1%, at least 2% at least 3%, at least 4%, at least 5%, at least 6%, at least 7%, at least 8%, at least 9%, at least 10%, or more of the total free fatty acids produced by the engineered microorganism. In some embodiments, the amount of the at least one unsaturated free fatty acid produced by the engineered microorganism is at least 1%, at least 2% at least 3%, at least 4%, at least 5%, at least 6%, at least 7%, at least 8%, at least 9%, at least 10%, or more of the total free fatty acids comprising at least 18 carbon atoms produced by the engineered microorganism. In some embodiments, the at least one unsaturated free fatty acid is selected from oleic acid, linoleic acid and α-linolenic acid. In some embodiments, the at least one unsaturated free fatty acid is selected from octadecatetraenoic acid, eicosatetraenoic acid, eicosapentaenoic acid (EPA), docosapentaenoic acid, and docosahexaenoic acid (DHA). In some embodiments, the amount of the at least one unsaturated free fatty acid produced by the engineered microorganism can be adjusted by adjusting the activity of at least one promoter operatively linked to at least one nucleic acid encoding an enzyme selected from acyl-lipid desaturase delta-9 (EC:1.14.19.1), acyl-lipid desaturase delta-12 (EC:1.14.19.6), acyl-lipid desaturase delta-15 (EC: 1.14.19.-), acyl-lipid desaturase delta-6 (EC: 1.14.19.3), acyl-lipid desaturase delta-4, acyl-lipid desaturase delta-5 bi-functional acyl-lipid desaturase delta-5/delta-6, $C_{20}$ acyl-lipid desaturase delta-8, and $C_{18-20}$ n-3 acyl-lipid desaturase), thioesterase (EC:3.1.2.14), acyl-lipid delta-6 elongase, polyunsaturated fatty acid (PUFA) elongase, acyl-lipid delta-9 elongase, EPA-polyketide synthase and DHA-polyketide synthase. For example, if the promoter is an inducible promoter such as a metal ion inducible promoter, the concentration of the metal ion in the culture media is adjusted to provide a desired amount of promoter activity, which in turn produces a desired amount of enzyme activity, which in turn produces a selected amount of the unsaturated free fatty acid.

Methods of extracting the fatty acids from the culture medium are known in the art. For instance, the fatty acids may be pipetted, filtered, and/or skimmed from the culture media. Alternatively, the fatty acids may be extracted from the medium using an organic solvent (e.g., hexanes, ether) followed by separation and removal of the organic solvent (e.g., distillation) to yield the fatty acids. In addition, the culture media may be treated to facilitate the extraction fatty acids dissolved in the media, for example, by changing the pH or salinity of the culture medium. The extraction procedure may be repeated in order to collect as much of the fatty acid produced as possible.

Non-secreted intracellular free fatty acids can be extracted following collection of cells by centrifugation using, for example, the Folch method for total lipids. Folch, J., M. Lees, et al., J Biol Chem 226(1): 497-509 (1957).

The unsaturated fatty acids made according to the methods disclosed herein can be isolated from impurities present or produced in the culture medium and/or separated from other saturated or unsaturated fatty acids. Methods for purifying and isolating unsaturated fatty acids are known in the art. For example, unsaturated fatty acids can be purified and/or isolated by distillation, metal ion complexation, low temperature crystallization, liquid and/or gas column chromatography, urea adduction, solvent extraction, and enzymatic methods.

In some embodiments a so-called green recovery system is used is used to harvest free fatty acids from a culture of an engineered microorganism disclosed herein. Green recovery systems are described in Liu et al., PNAS, Vol. 108, No. 17, pp. 6905-6908 (2011), which is incorporated herein by reference. In some embodiments of the system, lipolytic enzymes are used to degrade the membrane lipids into free fatty acids (FFA) with the collapse of cells. In some embodiments the Green Recovery system controls the synthesis of lipolytic enzymes using $CO_2$-limitation-inducible promoters, which induce expression of the lipolytic genes upon cessation of $CO_2$ aeration.

In some embodiments the lipolytic enzymes (EC 3.1.1) are selected from galactolipase and phospholipase B, which hydrolyze the carboxylic ester bonds to release the fatty acids from diacylglycerols. In some embodiments galactolipase (EC 3.1.1.26) is used to catalyze the hydrolysis of galactolipids by removing one or two fatty acids. In some embodiments phospholipase B, an enzyme with a combination of both Phospholipase A1 (EC 3.1.1.32) and Phospholipase A2 (EC 3.1.1.4) activities, is used to cleave acyl chains from both the sn-1 and sn-2 positions of a phospholipid.

In some embodiments a nickel inducible lysis system is used to control expression of the lipolytic enzyme. Examples include the promoter for a gene selected from ndhF3, sbtA, and cmpA.

E. Fatty Acid Compositions

The disclosed methods can be used to produce a fatty acid composition similar to that of a seed oil. Exemplary seed oils include, but are not limited to, coconut oil, cottonseed oil, flaxseed oil, grapeseed oil, corn (maize) oil, palm oil, palm olein, palm kernel oil, peanut oil, rapeseed oil, sesame seed oil, soybean oil and sunflower seed oil. In some embodiments, two or more fatty acids produced according to the methods disclosed herein are combined to produce a fatty acid composition similar to a seed oil. In some embodiments, 2, 3, 4, 5, 6, 7, 8, 9, 10, 11, 12, 13, 14 or 15 fatty acids produced according to the methods disclosed herein are combined to produce a fatty acid composition similar to a seed oil. In some embodiments the fatty acid composition further contains at least one fatty acid not produced by a method disclosed herein.

In some embodiments, the fatty acid composition produced according to the disclosed methods contains all the fatty acids that are known to be present in a seed oil. In other embodiments, the fatty acid composition produced according to the disclosed methods contains some but not all of the fatty acids that are known to be present in a seed oil; for example, the fatty acid composition in some embodiments contains only the predominant fatty acids or only those fatty acids that are present at or above a certain percentage (e.g., at or above 1%, 2%, 3%, 4%, 5%, 6%, 7%, 8%, 9%, 10%, 11%, 12%, 15%, 20%, 25%, 30%, 35%, 40%, 45% or 50%). Fatty acid compositions of common seed oils can be found, for example, in the Codex Alimentarius, published by the World Health Organization and the Food and Agriculture Organization of the United Nations (www.codexalimentarius.net), which is incorporated by reference in its entirety and for all purposes herein.

For example, the predominant fatty acids present in palm oil are palmitic acid (16:0), stearic acid (18:0), oleic acid (18:1) and linoleic acid (18:2), while other fatty acids may be present in lesser amounts (e.g., lauric acid (12:0), myristic acid (14:0), palmitoleic acid (16:1), margaric acid (17:0), linolenic acid (18:3), arachidic acid (20:0), eicosenoic acid (20:1), docosanoic acid (22:0)). In some embodiments, the fatty acid composition produced according to the disclosed methods contains two or more of palmitic acid (16:0), stearic acid (18:0), oleic acid (18:1), linoleic acid (18:2), lauric acid (12:0), myristic acid (14:0), palmitoleic acid (16:1), margaric acid (17:0), linolenic acid (18:3), arachidic acid (20:0), eicosenoic acid (20:1), and docosanoic acid (22:0) in proportions that approximate that of palm oil. In some embodiments, the fatty acid composition produced according to the disclosed methods contains two or more of palmitic acid (16:0), stearic acid (18:0), oleic acid (18:1) and linoleic acid (18:2) in proportions that approximate that of palm oil.

In another example, the predominant fatty acids present in soybean oil are palmitic acid (16:0), stearic acid (18:0), oleic acid (18:1), linoleic acid (18:2) and linolenic acid (18:3), while other fatty acids may be present in lesser amounts (e.g., lauric acid (12:0), myristic acid (14:0), palmitoleic acid (16:1), margaric acid (17:0), heptadecenoic acid (17:1), arachidic acid (20:0), eicosenoic acid (20:1), eicosadienoic acid (20:2), docosanoic acid (22:0), docosenoic acid (22:1), tetracosanoic acid (24:0)). In some embodiments, the fatty acid composition produced according to the disclosed methods contains two or more of palmitic acid (16:0), stearic acid (18:0), oleic acid (18:1), linoleic acid (18:2), linolenic acid (18:3), lauric acid (12:0), myristic acid (14:0), palmitoleic acid (16:1), margaric acid (17:0), heptadecenoic acid (17:1), arachidic acid (20:0), eicosenoic acid (20:1), eicosadienoic acid (20:2), docosanoic acid (22:0), docosenoic acid (22:1) and tetracosanoic acid (24:0) in proportions that approximate that of soybean oil. In some embodiments, the fatty acid composition produced according to the disclosed methods contains two or more of palmitic acid (16:0), stearic acid (18:0), oleic acid (18:1), linoleic acid (18:2) and linolenic acid (18:3) in proportions that approximate that of soybean oil.

In some embodiments, each of the two or more fatty acids present in the fatty acid composition is produced by a single recombinant organism. In some instances, the recombinant organism can produce each fatty acid in the desired proportion and amount to produce the replacement seed oil; in such instances, the fatty acids can be recovered from the recombinant organisms and used without the need to add or enrich any fatty acid component. In other instances, the recombinant organism can produce each fatty acid in proportions and amounts that are not similar to the targeted seed oil; in such instances, the fatty acids can be recovered from the recombinant organisms and combined with other fatty acids of recombinant or other origin to attain the desired proportions and amounts.

In another embodiment, multiple recombinant organisms produce one or more of the constituent fatty acids in the fatty acid composition; in such instances, the fatty acids are recovered and then combined with other fatty acids of recombinant or other origin to attain the desired proportions and amounts.

Linoleic acid is an essential fatty acid (an omega-6 essential fatty acid) that humans and other animals must ingest for good health. Insufficient linoleic acid in the diet can lead to adverse health effects, including hair loss and poor wound healing. In addition, linoleic acid has several industrial uses, including use in quick-drying oils in paints and varnishes, and use in cosmetics (due to its anti-inflammatory, anti-acne and moisture-retentive properties when applied to skin). α-Linolenic acid is also an essential fatty acid (an omega-3 essential fatty acid) for humans and other animals. Studies suggest α-linolenic acid may help prevent cardiovascular diseases such as coronary heart disease and stroke, and α-linolenic acid may have a neuroprotective effect.

Thus, in one embodiment, linoleic acid or α-linolenic acid produced according to the methods disclosed herein is formulated for administration to a human or other animal. In some embodiments, the linoleic acid or α-linolenic acid is formulated for oral administration, e.g., in the form of a tablet, capsule, or liquid. In other embodiments, the linolenic acid or α-linolenic acid is formulated for topical (e.g., dermal) administration.

In some embodiments, a formulation of linoleic acid or α-linolenic acid produced according to the methods disclosed herein includes one or more excipients, i.e., secondary ingredients that function to enable or enhance the delivery of a compound. For example, excipients may function to improve flow characteristics, product uniformity, stability, taste, or appearance, to ease handling and administration of dose, to improve the convenience of use, or to control bioavailability. Excipients are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995).

EXAMPLES

Example 1

Construction of Plasmids for Expression of Unsaturated Fatty Acids

The desA gene (acyl-lipid desaturase Δ12; slr1350; Genbank Accession No. NC_000911.1) from *Synechocystis* sp.

PCC 6803 was codon optimized for expression in *Escherichia coli* and synthesized (DNA 2.0). The codon optimized desA open reading frame is SEQ ID NO: 1. The desB gene (acyl-lipid desaturase Δ15; sll1441; Genbank Accession No. NC_000911.1) from *Synechocystis* sp. PCC 6803 was codon optimized for expression in *Escherichia coli* and synthesized (DNA 2.0). The codon optimized desB open reading frame is SEQ ID NO: 2. The desC gene (acyl-lipid desaturase Δ9; sll0541; Genbank Accession No. NC_000911.1) from *Synechocystis* sp. PCC 6803 was codon optimized for expression in *Escherichia coli* and synthesized (DNA 2.0). The codon optimized desC open reading frame is SEQ ID NO: 3.

A truncated version of the *E. coli* tesA (acyl-CoA thioesterase I; b0494) was PCR amplified from the *E. coli* BL21(DE3) (Novagen) chromosome using primers 5'-CATGCTCCATGGCGGACACGTTATTGATTC-3' (SEQ ID NO: 4) and 5'-CATGCTGCGGCCGCTTATGAGTCATGATTTACTAAAGG-3' (SEQ ID NO: 5). The truncated tesA gene, henceforth referred to as "'tesA", was cloned into MCS1 of pCDFDuet-1 (Novagen) using NcoI and NotI, generating pCDFDuet-'tesA. desC was cloned into MCS2 of pCDFDuet-'tesA using NdeI and XhoI, generating pCDFDuet-'tesA-desC. desA was cloned into MCS1 of pETDuet-1 (Novagen) using BbsI/NcoI and NotI, generating pETDuet-desA. desB was cloned into MCS2 of pETDuet-desA using NdeI and XhoI, generating pETDuet-desA-desB.

The pAQ1-shuttle contains a left insertion site (SEQ ID NO: 6) and a right insertion site (SEQ ID NO: 7) for the fragment to be inserted into pAQ1 of *Synechococcus* sp. PCC 7002, spectinomycin selection marker and p(cpc) promoter from *Synechocystis* sp. PCC 6803 to drive the expression of genes of interest.

The pAQ3-shuttle contains a left insertion site (SEQ ID NO: 8) and a right insertion site (SEQ ID NO: 9) for the fragment to be inserted into pAQ3 of *Synechococcus* sp. PCC 7002, kanamycin selection marker and p(cpc) promoter from *Synechocystis* sp. PCC 6803 to drive the expression of genes of interest.

The pAQ1-desA-desB plasmid is constructed by first PCR-amplifying a desA-desB fragment from pETDuet-desA-desB using the forward primer (5'-GACTGAGAAGACTA CATGACCGCCACGATTC-3') (SEQ ID NO: 10) and reverse primer (5'-TCAGTCGGATCCTTACGGCTTTTTCTGGTAACCG-3') (SEQ ID NO: 11), then cutting with restriction enzymes BbsI and BamHI, and then cloned into the pAQ1-shuttle vector cut with NcoI and BamHI to insert desA-desB downstream of the p(cpc) promoter sequence.

The pAQ3-tesA'-desC plasmid is constructed by first PCR amplifying a tesA'-desC fragment from pCDFDuet-tesA'-desC using the forward primer (5'-GACTGAGAAGACAC-CATGGCGGACACGTTATTGATTC-3') (SEQ ID NO: 12) and reverse primer (5'-TCAGTCGGATCCTTAG-GCTTTGTTCGCCATCGC-3') (SEQ ID NO: 13), then cutting with restriction enzymes BbsI and BamHI, and then cloned into the pAQ1-shuttle vector cut with NcoI and BamHI to insert desA-desB downstream of the p(cpc) promoter sequence.

Figure 2A:
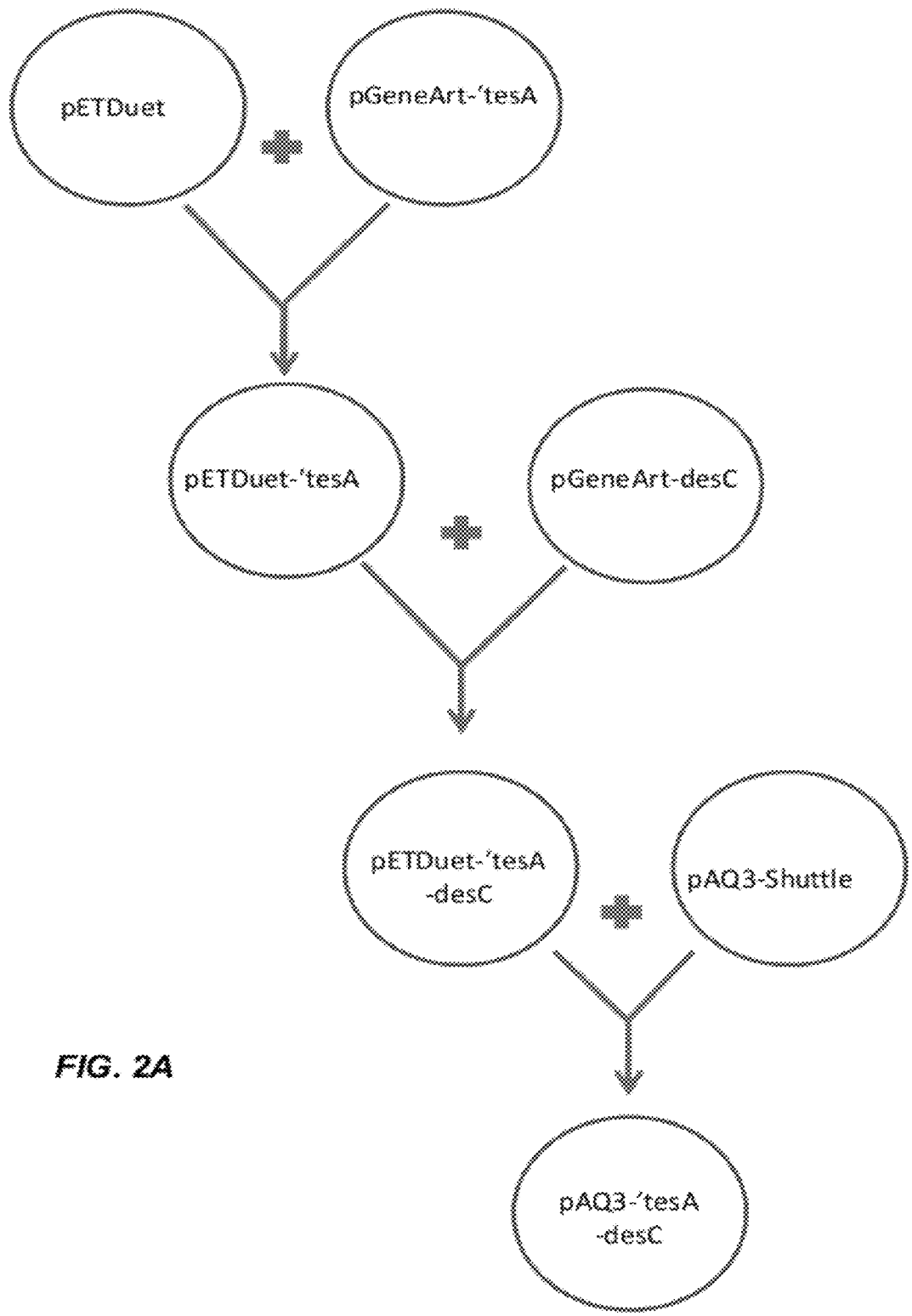
FIG. 2A and 2B show the cloning steps and intermediate plasmids used to create the plasmids pAQ3-tesA'-desC (2A) and pAQ1-desA-desB (2B).
Figure 2B:
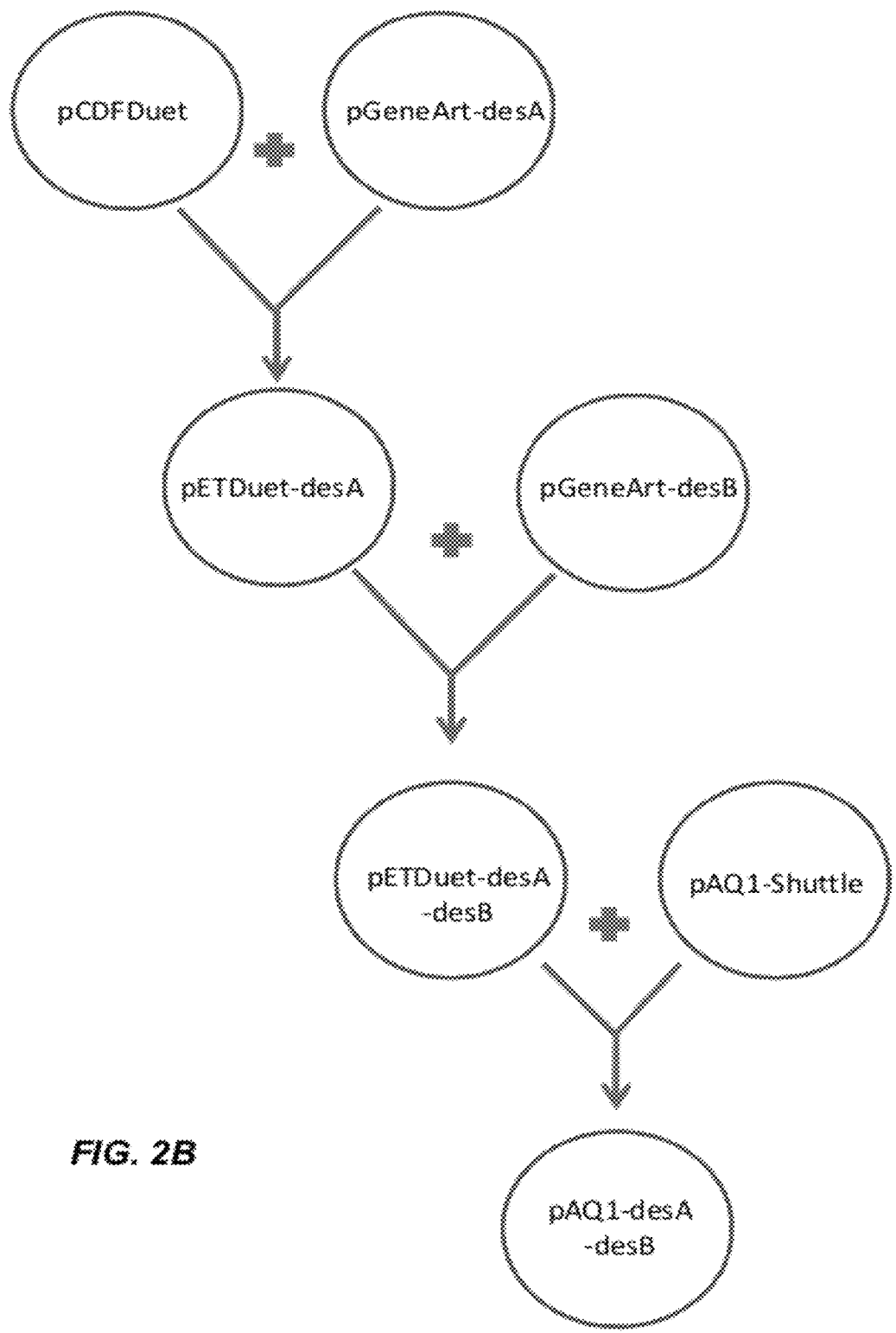

Construction of the various plasmids is shown schematically in FIGS. 2A and 2B.

Example 2

Production of Unsaturated Fatty Acids in *E. coli*

Plasmids were transformed into *E. coli* BL21(DE3) and selected on 50 mg/l spectinomycin (for the pCDFDuet-1 derivatives) and 100 mg/l carbenicillin (for the pETDuet-1 derivatives). A single colony was picked and stored as a glycerol stock at −80° C., to serve as a master cell stock. A working cell bank was created from this master cell stock in EZ-Rich medium (Teknova) supplemented with 10% glycerol (v/v).

10 ml EZ-Rich production cultures (in a 125 ml baffled flask) were inoculated to $OD_{600\,nm}$=0.05 with a working cell stock and grown at 22-37° C. and 250 rpm. Cultures were grown to $OD_{600\,nm}$≈0.6-0.8 and heterologous gene-expression was initiated with 1 mM isopropyl β-D-1-thiogalactopyranoside (IPTG) and grown for another 2-16 hr until harvest. Upon harvesting, a 1 ml aliquot was centrifuged; the supernatant was decanted, and stored at −20° C. until fatty acid and gene-expression analyses.

Example 3

Extraction of Fatty Acids Produced in *E. coli* and Quantification Using HPLC

The pellet was then resuspended in 100 ul of chloroform:methanol (2:1 vol/vol) and incubated at 55° C. for 10 minutes. The resuspended lysed cells were centrifuged at 8000 rpm for 5 minutes and the supernatant was extracted and dried in room temperature. It was then resuspended in 100 ul of methanol followed by 100 ul of 1 mg/ml PDAM (1-Pyrenyldiazomethane suspended in ethyl acetate). The derivatization reaction was allowed to proceed for at least 90 minutes at room temperature in an amber walled HPLC vial. The fatty acid standards were diluted in methanol at different concentrations and derivatized using PDAM in similar conditions.

After derivatization, 10 ul of derivatized fatty acid samples were injected onto a Zorbax Eclipse XDB-C18 reverse phase column (4.6×150 mm, 5 μm) maintained at 30° C. Samples were eluted with an Agilent 1100 series HPLC system at 1 ml/min with Buffer A: $H_2O$ and Buffer B: Acetonitrile, as 90-100% Buffer B in 60 minutes, held at 100% buffer B for 1 minute, 100-90% Buffer B in 1 minute, and re-equilibrated at 90% buffer B for 8 minutes. Fluorescence detection was determined using an Agilent G1321A fluorescent detector with PMT gain=10, peak width response >0.05 min (1 s Fast), at excitation=340 nm, emission=395 nm.

Figure 6:
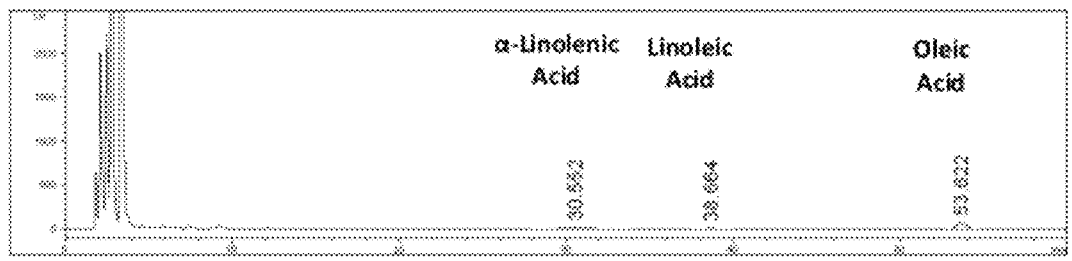
FIG. 6 shows that *E. coli* expressing recombinant DesA, DesB, and DesC produce oleic acid, linoleic acid, and alpha-linolenic acid.
Figure 7:
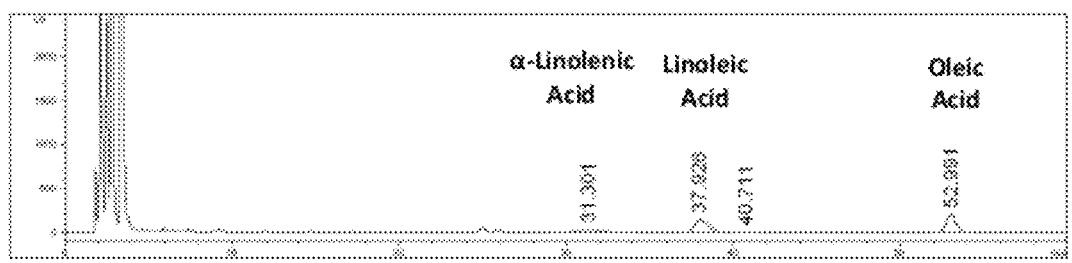
FIG. 7 shows that expression of recombinant TesA in combination with recombinant DesA, DesB, and DesC in *E. coli* increases the levels of free fatty acids produced. An unknown peak that appears to be a 16:1 or 14:0 free fatty acid also appears.

FIG. 6 shows the extracted sample from *E. coli* overexpressing DesA, DesB and DesC. As shown, detectable levels of oleic acid (18:1), linoleic acid (18:2), and alpha-linolenic acid (18:3) were observed. FIG. 7 shows the extracted sample from *E. coli* overexpressing DesA, DesB, DesC and TesA'. As shown, co-expression of TesA' increased the levels of free fatty acids produced.

Figure 3:
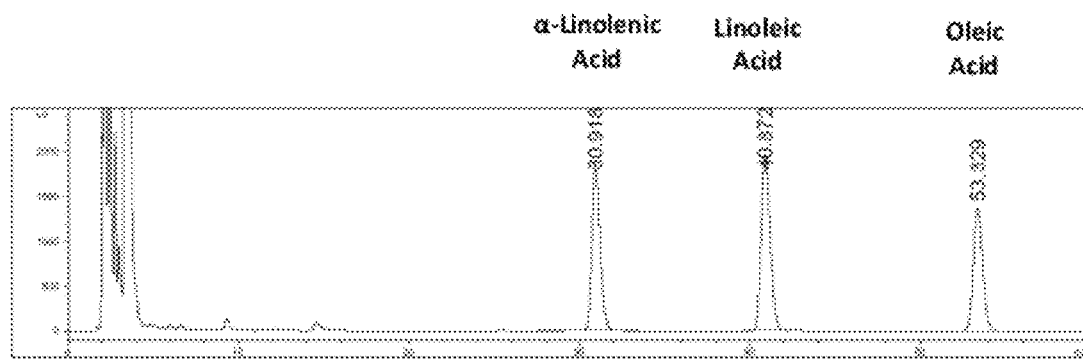
FIG. 3 shows HPLC peaks generated by a standard mixture of oleic acid, linoleic acid, and alpha-linolenic acid used as a positive control.
Figure 4:
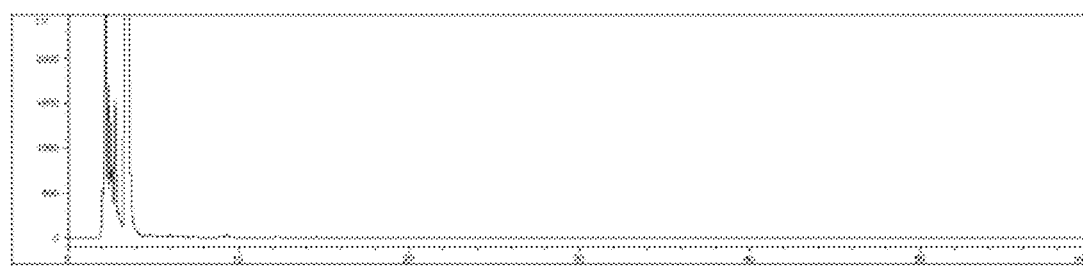
FIG. 4 shows the absence of HPLC peaks generated by methanol as a negative control.
Figure 5:
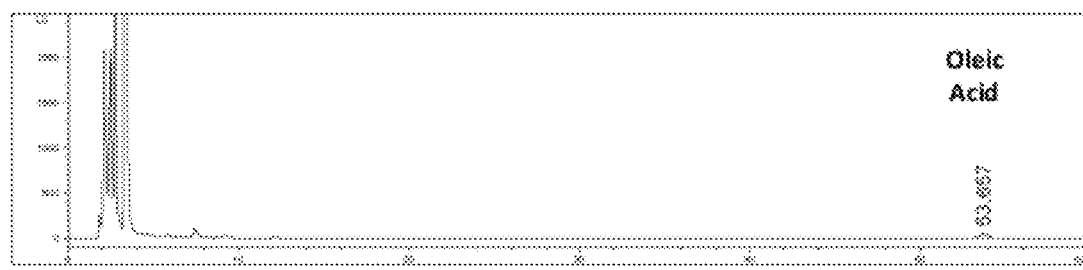
FIG. 5 shows that *E. coli* natively makes oleic acid.

For comparison, FIG. 3 shows a HPLC run of oleic acid (18:1), linoleic acid (18:2), and alpha-linolenic acid (18:3) standards purchased from Sigma® (injecting 10 ul of a 20 uM solution of each). FIG. 4 shows a HPLC run of 10 ul methanol, showing that there is no residual from a previous run. FIG. 5 shows the extracted sample from wild type *E. coli* to demonstrate that it only produces oleic acid but not linoleic and alpha-linolenic acid.

Example 4

Production of Unsaturated Fatty Acids in *Synechococcus* sp. PCC 7002

To generate the *Synechococcus* sp. PCC 7002 strains with expression of the desA, desB, tesA' and desC genes, DNAs of the gene expression shuttle vectors were transformed into cells of *Synechococcus* sp. PCC 7002. For each transformation, 3 ug DNA of the pAQ1-desA-desB plasmid and the and pAQ3-tesA'-desC plasmid were added to 2 ml of *Synechococcus* sp. PCC 7002 liquid culture at $OD_{730}$ 2.0 and incubated for 6 hours in 75 micromol/meter$^2$/sec light intensity, 2% $CO_2$ and shaking at 200 rpm. After incubation, 400 ul of cell transformation culture was spread onto the A$^+$ agar plates with addition of 50 ug/ml Spectinomycin and 50 ug/ml Kanamycin. Transformant colonies were visible in a week. For segregation, colonies were picked and streaked on A$^+$ agar plates containing 100 ug/ml Spectinomycin and 100 ug/ml Kanamycin for segregation screening. This colony restreaking procedures was repeated three or more times once a week.

After the segregation, colonies of the new *Synechococcus* sp. PCC 7002 strains with expression of desA, desB, tesA' and desC genes were restreaked and inoculated into the A$^+$ liquid media with addition of the spectinomycin (100 ug/ml) and kanamycin (100 ug/ml). The tubes with 5 ml liquid culture were grown in the light incubator with 75 micromol/meter$^2$/sec light intensity, 2% $CO_2$ and shaking at 200 rpm for 2 days. When cells were grown to their late exponential growth phase, cells from 5 ml culture at about 1-OD were harvested through centrifugation at 8000 rpm. The cell pellet was used for extraction of fatty acids and identification of different unsaturated fatty acids in whole cell extract. As a control, cells of the *Synechococcus* sp. PCC 7002 wild-type strain were grown up under the same growth conditions.

Example 5

Extraction of Fatty Acids Produced in *Synechococcus* sp. PCC 7002 and Quantification Using HPLC The pellet was resuspended in 100 ul of chloroform:methanol (2:1 vol/vol) and incubated at 55° C. for 10 minutes. The resuspended lysed cells were centrifuged at 8000 rpm for 5 minutes and the supernatant was extracted and dried in room temperature. The dried extract was then resuspended in 100 ul of methanol followed by 100 ul of 1 mg/ml PDAM (1-Pyrenyldiazomethane suspended in ethyl acetate). The derivatization reaction was allowed to proceed for at least 90 minutes at room temperature in an amber walled HPLC vial. The fatty acid standards were diluted in methanol at different concentrations and derivatized using PDAM using similar conditions.

After derivatization, 10 μl of derivatized fatty acid samples were injected onto a Zorbax Eclipse XDB-C18 reverse phase column (4.6×150 mm, 5 μm) maintained at 25° C. Samples were eluted with an Agilent 1100 series HPLC system at 1 ml/min with Buffer A: $H_2O$ and Buffer B: Acetonitrile, as 95-100% Buffer B in 60 minutes, held at 100% buffer B for 10 minute, 100-90% Buffer B in 0.01 minute, and re-equilibrated at 90% buffer B for 10 minutes. Fluorescence detection was determined using an Agilent G1321A fluorescent detector with PMT gain=10, peak width response >0.05 min (1 s Fast), at excitation=340 nm, emission=395 nm.

Figure 8:
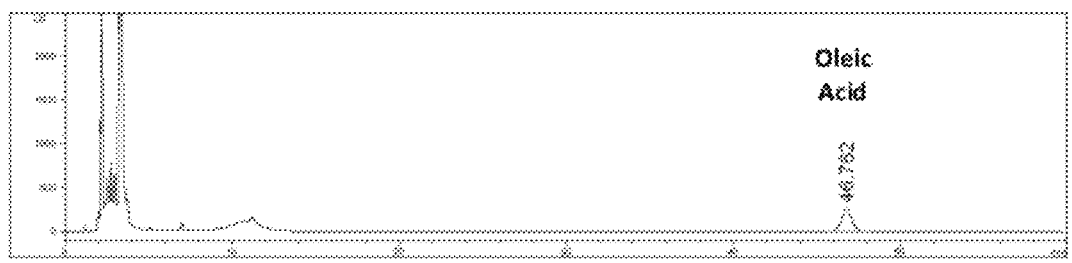
FIG. 8 shows an HPLC peak generated by a standard mixture of oleic acid used as a positive control.
Figure 9:
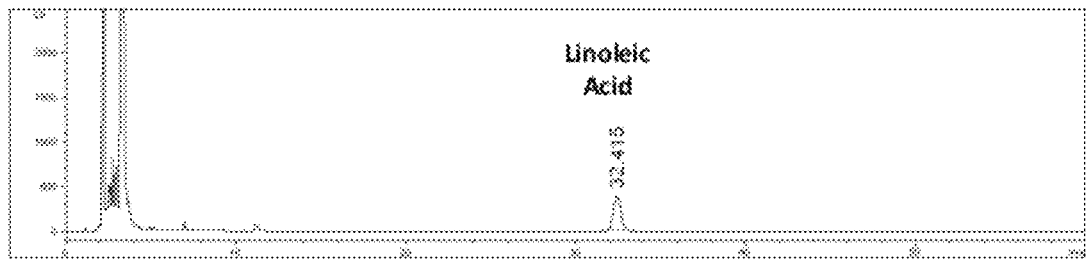
FIG. 9 shows an HPLC peak generated by a standard mixture of linoleic acid used as a positive control.
Figure 10:
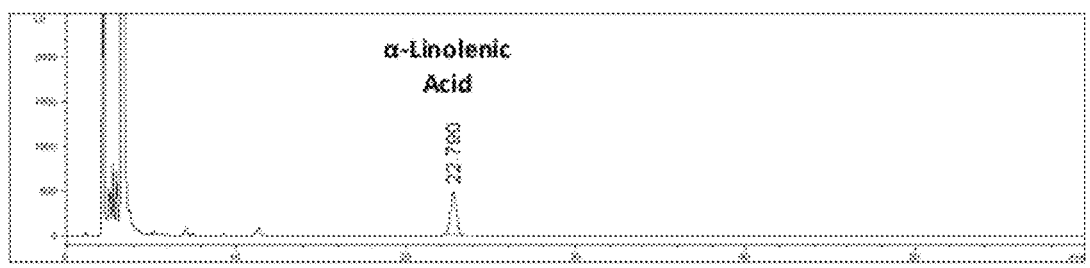
FIG. 10 shows an HPLC peak generated by a standard mixture of alpha-linolenic acid used as a positive control.
Figure 12:
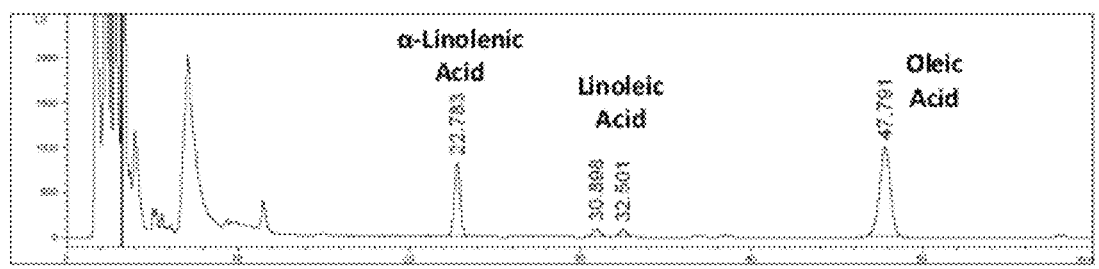
FIG. 12 shows that *Synechococcus* sp. PCC 7002 transformed with recombinant TesA, DesA, DesB, and DesC produces increased levels of oleic acid, linoleic acid, and alpha-linolenic acid.

The results are presented in FIG. 12. Based on the known concentration of each standard fatty acid and corresponding observed peak area for each compound in HPLC (FIGS. 8-10), the peak area/molar quantites are calculated for each fatty acid. Then the actual concentration of the sample is calculated based on the observed peak area and converting them into molar quantities based on the standards peak area/molar quantities. Finally based on the molecular weight of each fatty acid, the corresponding concentration in gram/liter of each fatty acid extracted from each sample is calculated.

Figure 11:
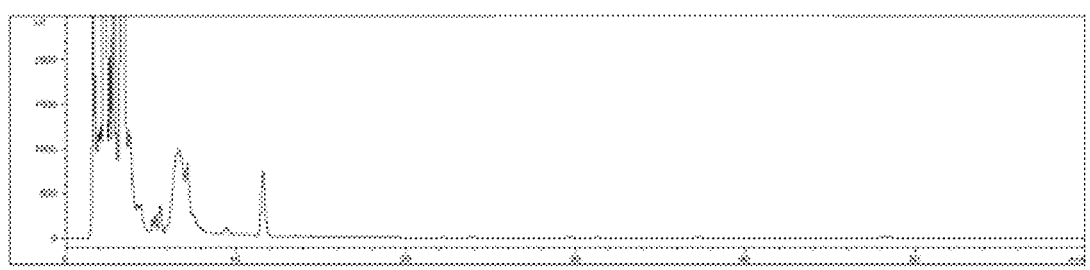
FIG. 11 shows that wild type cyanobacteria do not make detectable quantities of levels of oleic acid, linoleic acid, and alpha-linolenic acid.

Based on the standard, 1.88 mg/L of α-linoleic acid, 0.067 mg/l linoleic acid and 4.62 mg/l oleic acid was produced in 5 ml of engineered cynobacterial strain cell culture of OD 1, compared to 0 mg/L of α-linoleic acid, 0 mg/l linoleic acid and 0.2 mg/l oleic acid in 5 ml of wild type cynobacterial strain when grown at 37° C. (FIG. 11).

The invention claimed is:

1. A method for producing an unsaturated free fatty acid comprising at least 18 carbon atoms, the method comprising:
   culturing an engineered microorganism in a culture medium, wherein the engineered microorganism comprises at least one recombinant acyl-lipid desaturase specific for a substrate comprising at least 18 carbon atoms, and wherein production of acyl-ACP synthetase (EC:6.2.1.20) is reduced or eliminated in the engineered microorganism, and
   wherein the amount of the unsaturated free fatty acid comprising at least 18 carbon atoms produced by the engineered microorganism is increased relative to the amount of the unsaturated free fatty acid comprising at least 18 carbon atoms produced by an otherwise identical microorganism lacking the at least one recombinant acyl-lipid desaturase.

2. The method of claim 1, wherein the at least one recombinant acyl-lipid desaturase is selected from acyl-lipid desaturase delta-9 (EC:1.14.19.1), acyl-lipid desaturase delta-12 (EC:1.14.19.6), and acyl-lipid desaturase delta-15 (EC:1.14.19.-).

3. The method of claim 2, wherein the unsaturated free fatty acid comprising at least 18 carbon atoms is selected from oleic acid, linoleic acid and α-linolenic acid.

4. The method of claim 1, wherein the at least one recombinant acyl-lipid desaturase is a recombinant acyl-lipid desaturase delta-9 (EC:1.14.19.1), and
   wherein the engineered microorganism produces oleic acid, and the production of oleic acid is increased in the engineered microorganism relative to production of oleic acid by an otherwise identical microorganism lacking the recombinant acyl-lipid desaturase delta-9 (EC: 1.14.19.1).

5. The method of claim 1, wherein the engineered microorganism
   comprises a recombinant acyl-lipid desaturase delta-12 (EC:1.14.19.6), and
   wherein the engineered microorganism produces linoleic acid, and the production of linoleic acid is increased in the engineered microorganism relative to production of linoleic acid by an otherwise identical microorganism lacking the recombinant acyl-lipid desaturase delta-12 (EC:1.14.19.6).

6. The method of claim 1, wherein the engineered microorganism
   comprises a recombinant acyl-lipid desaturase delta-15 (EC:1.14.19.-), and
   wherein the engineered microorganism produces α-linolenic acid, and the production of α-linolenic acid is increased in the engineered microorganism relative to production of α-linolenic acid by an otherwise identical microorganism lacking the recombinant acyl-lipid desaturase delta-15 (EC:1.14.19.-).

7. The method of claim 1, wherein the engineered microorganism
comprises a recombinant acyl-lipid desaturase delta-12 (EC:1.14.19.6) and a recombinant acyllipid desaturase delta-15 (EC:1.14.19.-),
wherein the engineered microorganism produces α-linolenic acid, and the production of α-linolenic acid is increased in the engineered microorganism relative to production of α-linolenic acid by an otherwise identical microorganism lacking at least one of the recombinant acyl-lipid desaturase delta-12 (EC:1.14.19.6) and the recombinant acyl-lipid desaturase delta-15 (EC:1.14.19.-).

8. The method of claim 7, wherein the engineered microorganism further
comprises a recombinant acyl-lipid desaturase delta-9 (EC:1.14.19.1),
wherein the production of α-linolenic acid is increased in the engineered microorganism relative to production of α-linolenic acid by an otherwise identical microorganism lacking at least one of the recombinant acyl-lipid desaturase delta-9 (EC:1.14.19.1), the recombinant acyllipid desaturase delta-12 (EC:1.14.19.6) and the recombinant acyl-lipid desaturase delta-15 (EC:1.14.19.-).

9. The method of claim 1, wherein the engineered microorganism
comprises a recombinant acyl-lipid desaturase delta-9 (EC:1.14.19.1), a recombinant acyl-lipid desaturase delta-12 (EC:1.14.19.6) and a recombinant acyl-lipid desaturase delta-15 (EC:1.14.19.-),
wherein the engineered microorganism produces oleic acid, linoleic acid and α-linolenic acid, and the production of at least one of oleic acid, linoleic acid and α-linolenic acid is increased in the engineered microorganism relative to the production of the corresponding oleic acid, linoleic acid and α-linolenic acid by an otherwise identical microorganism lacking at least one of the recombinant acyl-lipid desaturase delta-9 (EC:1.14.19.1), the recombinant acyl-lipid desaturase delta-12 (EC:1.14.19.6) and the recombinant acyl-lipid desaturase delta-15 (EC:1.14.19.-).

10. The method of claim 1, wherein the engineered microorganism comprises recombinant subunits accB, accC, accD, and accA of the acetyl-CoA carboxylase enzyme (EC:6.4.1.2).

11. The method of claim 1, wherein the engineered microorganism further comprises a recombinant thioesterase (EC:3.1.2.14).

12. The method of claim 11, wherein the recombinant thioesterase (EC:3.1.2.14) is localized to the cytosol.

13. The method of claim 1, wherein the engineered microorganism is a cyanobacterium.

14. The method of claim 1, wherein the engineered microorganism is *Escherichia coli*.

15. An engineered microorganism comprising at least one recombinant nucleic acid encoding an acyl-lipid desaturase specific for a substrate comprising at least 18 carbon atoms, and wherein the engineered microorganism comprises at least one genetic modification that reduces or eliminates production of acyl-ACP synthetase (EC:6.2.1.20).

16. The engineered microorganism of claim 15, wherein the engineered microorganism further comprises a recombinant nucleic acid encoding a thioesterase (EC:3.1.2.14).

17. The engineered microorganism of claim 15, wherein the at least one acyl-lipid desaturase specific for a substrate comprising at least 18 carbon atoms is selected from acyl-lipid desaturase delta-9 (EC:1.14.19.1), acyl-lipid desaturase delta-12 (EC:1.14.19.6), and acyl-lipid desaturase delta-15 (EC:1.14.19.-).

18. The engineered microorganism of claim 15, wherein the engineered microorganism further comprises one or more recombinant nucleic acid that together encode subunits accB, accC, accD, and accA of the acetyl-CoA carboxylase enzyme (EC:6.4.1.2).

19. The engineered microorganism of claim 16, wherein the recombinant nucleic acid encoding a thioesterase (EC:3.1.2.14) encodes a recombinant thioesterase (EC:3.1.2.14) localized to the cytosol of the engineered microorganism.

20. The engineered microorganism of claim 15, wherein the engineered microorganism is a cyanobacterium.

21. The engineered microorganism of claim 15, wherein the engineered microorganism is *Escherichia coli*.

* * * * *

SEQUENCE LISTING

<160> NUMBER OF SEQ ID NOS: 13

<210> SEQ ID NO 1
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgaccgcca cgattccgcc gctgaccccg accgttaccc cgagcaaccc agaccgccct      60
attgccgacc tgaaattgca agatatcatc aagaccctgc cgaaagagtg tttcgaaaag     120
aaagcgtcca aggcgtgggc gtcggtcctg attaccctgg gtgcgattgc agtcggttac     180
ttgggcatca tctacctgcc gtggtactgc ctgccgatca cttggatctg gacgggtact     240
gccctgacgg gcgcttttgt ggtcggtcac gactgcggtc atcgcagctt cgcaaagaaa     300
cgttgggtga atgacctggt gggtcatatc gcattcgcgc cgttgatcta tccgtttcat     360
agctggcgtc tgttgcacga tcaccatcac ctgcacacca acaagattga agttgataac     420
gcatgggacc cgtggtccgt tgaggccttc caagcgagcc cggcaattgt ccgtctgttc     480
taccgtgcga ttcgtggccc gttctggtgg accggctcca tttttcactg gagcctgatg     540
catttcaagt tgtctaactt cgcgcagcgt gatcgtaaca aagtgaaact gagcatcgcg     600
```

| | |
|---|---|
| gtggtatttc tgtttgccgc gattgctttc ccggcactga ttatcaccac gggtgtctgg | 660 |
| ggttttgtta agttctggct gatgccgtgg ctggtttatc acttttggat gtctacgttc | 720 |
| accatcgtgc atcatacgat cccggaaatt cgctttcgcc ctgcggcgga ttggagcgcg | 780 |
| gctgaggctc agctgaatgg tacggttcat tgcgattacc cgcgttgggt tgaggttctg | 840 |
| tgtcacgaca tcaacgtgca cattccgcac cacctgagcg tggccatccc gagctataat | 900 |
| ctgcgtctgg cacacggcag cttgaaagag aattggggtc cgtttctgta cgagcgtacc | 960 |
| ttcaattggc aactgatgca acagattagc ggtcagtgtc acctgtatga cccagaacac | 1020 |
| ggctatcgca cctttggcag cctgaagaaa gtctaa | 1056 |

<210> SEQ ID NO 2
<211> LENGTH: 1080
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| atgcgcctgg aaatcagctc gcctcaaacc aaactgccat acccgaaaac cgaagaactg | 60 |
| ccgtttaccc tgcaagagct cgcaatgcg attccggcag attgttttga accgagcgtc | 120 |
| gtccgtagcc tgggttattt cttctggat gtgggtctga ttgctggttt ttacgctctg | 180 |
| gccgcctacc tggactcttg gttttctat ccgatcttct ggctgatcca gggtacgttg | 240 |
| ttctggtccc tgttcgtcgt tggtcacgat gccggtcacg gcagctttag caagtccaaa | 300 |
| acgctgaaca actggatcgg tcatttgagc cataccccaa ttttggtgcc gtaccacggt | 360 |
| tggcgtatca gccaccgcac ccatcacgcg aataccggca atattgacac cgacgagagc | 420 |
| tggtatccgg tttctgaaca gaagtataat cagatggcgt ggtatgagaa gctgctgcgt | 480 |
| ttctatctgc cgctgatcgc gtacccgatt tacttgtttc gtcgtagccc gaatcgtcag | 540 |
| ggtagccact tcatgccggg ctcgcctctg tttcgtccgg gcgagaaagc cgctgttctg | 600 |
| acgagcacct tcgcgctggc agcgtttgtg ggtttcctgg gcttcctgac gtggcagttc | 660 |
| ggctggctgt ttctgttgaa attctacgtt gccccgtatc tggtgtttgt tgtgtggctg | 720 |
| gacttggtga ctttttctgca tcacacggag gataacatcc cgtggtatcg tggcgacgac | 780 |
| tggtattttc tgaagggtgc gctgtctacc attgaccgcg attatggttt catcaatccg | 840 |
| attcatcacg acattggcac tcacgtcgca catcacattt tcagcaacat gccgcattac | 900 |
| aagctgcgtc gtgcaaccga ggcgattaag ccaatcttgg gtgagtatta ccgctactcc | 960 |
| gatgaaccga tctggcaagc attcttcaaa agctactggg cgtgccactt cgttccgaac | 1020 |
| caaggtagcg cgctctacta ccaaagcccg agcaacggcg gttaccagaa aaagccgtaa | 1080 |

<210> SEQ ID NO 3
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| atgctgaatc cgctgaacat cgaatacctg tacctgagca aactgtttga caacagcctg | 60 |
| atcgtgttca ataagcgtca gctgtttcgc ttcttcgttc gtttcttctt tatgactgcg | 120 |
| gctctgccga atgatagcaa gccgaaactg accccagcct ggaccgtgat cttcttttc | 180 |

```
acgagcattc acctggttgc gctgctggcg ttcctgccgc agttttctc ttggaaggcg      240 gtaggtatgg cattcttgct gtatgttatt acgggcggta tcggtattac cctgggtttc     300
catcgctgta tcagccatcg ttcgttcaat gtcccgaagt ggctggaata catctttgtc     360
atttgcggca ccctggcatg tcaaggcggc gtgtttgagt gggttggtct gcaccgcatg     420
catcacaagt tcagcgatac caccccggac ccgcatgatt ccaacaaagg cttctggtgg     480
agccacattg ttggatgat gtttgagatt ccggcgaaag cggatatccc gcgttacacg      540
aaggacattc aggacgacaa gttttatcag ttctgccaaa acaatctgat cctgatccag     600
gtcgcactgg gcctgatctt gttcgctttg ggcggttggc cgtttgttat ttgggggtatt    660 ttcgttcgtc tggtgtttgt ttttcatttc acgtggtttg tgaatagcgc aacccacaaa     720
tttggctatg tgagccacga gagcaacgat tatagccgca actgctggtg ggtcgcgttg    780
ctgaccttcg gtgagggttg gcacaacaat caccatgcat accaatactc tgcccgtcac     840
ggtctgcaat ggtgggaggt cgatctgacc tggatgacta tcaaatttct gtccttgttg     900
ggtctggcca aagacattaa gctgcctccg gaaacggcga tggcgaacaa agcctaa        957
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
catgctccat ggcggacacg ttattgattc                                       30
```

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
catgctgcgg ccgcttatga gtcatgattt actaaagg                              38
```

<210> SEQ ID NO 6
<211> LENGTH: 514
<212> TYPE: DNA
<213> ORGANISM: Synechococcus sp.

<400> SEQUENCE: 6

```
tggggttttc tcgtgtttag gcagcatctt gatccgcctc atcattgtta tagacttcga      60
gcaaatctcg taaaacaagc tcccggatat agtcgctgaa atttaagcct tgctcattgg     120
cttttttagt agccgcgctg tacatgagtg ggggaaaacg aaccgcgctc gctgatttta     180
aattcttatt cggtctagtc gtcatgggat cgcctaagaa agtctctatc attttacagt     240
atccaaaaga tttgacaccc ccattcatgg tggtattttt tcttttcctt ttccccatag     300
cactgtggct agcaataaag ctatgggcga tccctacatt tattctgtag caccaacgct     360
acagcccctt aatttcctgt ggataaacag tgtggaaatt gagaagaaca catgagaatt     420
tgtccagttt tatttgatg gttattttttt gcggttgctt tttaagggaa ttgtgcgtgt     480
ggtttccagt ccccatctgt gcataagaga aagg                                 514
```

<210> SEQ ID NO 7
<211> LENGTH: 387
<212> TYPE: DNA
<213> ORGANISM: Synechococcus sp.

<400> SEQUENCE: 7

```
tcgacgcctc ctgaataaat ctatttatac aggggttgga cacggcccct aattttgctt      60
ggtcacgctg taaccaatga gcaaagacct tttcgcgctg atcgttaggg gcgatcgcct     120
catagacccg ctgacggtta tcccgcgatc caaagcgccc cttgtattcc aatttccggt     180
caagcttgcc taggagcgcc tgagcaattt cgagcgggct cattttgtcg gtgatcgttc     240
tgccaagaat ccacttgatc ggcttggcat accgcaaaca attttccttg aacccttcaa     300
ggctcgcccc ggtgaatgtc acccctggtt ttaagaactg atggatgttg agtagctcta     360
acaggtgaat ctttggtgag aggcatg                                         387
```

<210> SEQ ID NO 8
<211> LENGTH: 524
<212> TYPE: DNA
<213> ORGANISM: Synechococcus sp.

<400> SEQUENCE: 8

```
tggcgacctg cccgacctct tcaaggatga agccgaacta cgcaccatct gggggaaacc      60
cgatacccgt aaatcgttcc tgaccggact cgcggaaaaa ggctacgtg acacccaact     120 gaaggcgatc gcacgcattg ccgaagcgga aaaagtgat gtctatgatg tcctgacttg     180
ggttgcctac aacaccaaac ccattagcag agaagagcga gtaattaagc atcgagatct     240
gattttctcg aagtacaccg gaaagcagca agaattttta gattttgtcc tagaccaata     300
cattcgagaa ggagtggagg aacttgatcg ggggaaactg cctaccctca tcgaaatcaa     360
ataccaaacc gttaatgaag gtttagtgat cttgggtcag gatatcggtc aagtattcgc     420
agattttcag gcggatttat ataccgaaga tgtggcataa aaaaggacgg cgatcgccgg     480
gggcgttgcc tgccttgaac gaggaattgc aggcagcagc cgcg                     524
```

<210> SEQ ID NO 9
<211> LENGTH: 514
<212> TYPE: DNA
<213> ORGANISM: Synechococcus sp.

<400> SEQUENCE: 9

```
tcgacacgag aaagagttat gacaaattaa aattctgact cttagattat ttccagagag      60
gctgattttc ccaatctttg ggaaagccta agttttaga ttctatttct ggatacatct     120
caaaagttct ttttaaatgc tgtgcaaaat tatgctctgg tttaattctg tctaagagat     180
actgaataca acataagcca gtgaaaattt tacggctgtt tctttgatta atatcctcca     240
atacttctct agagagccat tttccttta acctatcagg caatttaggt gattctccta     300
gctgtatatt ccagagcctt gaatgatgag cgcaaatatt tctaatatgc gacaaagacc     360
gtaaccaaga tataaaaaac ttgttaggta attggaaatg agtatgtatt ttttgtcgtg     420
tcttagatgg taataaattt gtgtacattc tagataactg cccaaaggcg attatctcca     480
aagccatata tgacggcggt agtagagggc atgc                                 514
```

<210> SEQ ID NO 10
<211> LENGTH: 31
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 10
gactgagaag actacatgac cgccacgatt c                                   31

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcagtcggat ccttacggct ttttctggta accg                                34

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gactgagaag acaccatggc ggacacgtta ttgattc                             37

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcagtcggat ccttaggctt tgttcgccat cgc                                 33
```